(12) United States Patent
Park et al.

(10) Patent No.: US 9,321,751 B2
(45) Date of Patent: Apr. 26, 2016

(54) PIPERINE DERIVATIVES AND USES THEREOF

(71) Applicant: INDUSTRY-ACADEMIC COOPERATION FOUNDATION, YONSEI UNIVERSITY, Seoul (KR)

(72) Inventors: Tae Sun Park, Seoul (KR); Nak Shin Jeong, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 14/374,532

(22) PCT Filed: Dec. 27, 2012

(86) PCT No.: PCT/KR2012/011548
§ 371 (c)(1),
(2) Date: Jul. 25, 2014

(87) PCT Pub. No.: WO2013/115486
PCT Pub. Date: Aug. 8, 2013

(65) Prior Publication Data
US 2014/0371271 A1 Dec. 18, 2014

(30) Foreign Application Priority Data

Jan. 31, 2012 (KR) .................. 10-2012-0009362

(51) Int. Cl.
| | | |
|---|---|---|
| *C07D 317/58* | (2006.01) | |
| *C07D 317/60* | (2006.01) | |
| *C07D 317/62* | (2006.01) | |
| *C07D 295/192* | (2006.01) | |
| *C07D 405/12* | (2006.01) | |
| *C07D 211/06* | (2006.01) | |

(52) U.S. Cl.
CPC ............ *C07D 405/12* (2013.01); *C07D 211/06* (2013.01); *C07D 295/192* (2013.01); *C07D 317/58* (2013.01); *C07D 317/60* (2013.01); *C07D 317/62* (2013.01)

(58) Field of Classification Search
CPC .. C07D 317/60; C07D 317/62; C07D 317/58; C07D 295/192; C07D 405/12; C07D 211/06
See application file for complete search history.

(56) References Cited

U.S. PATENT DOCUMENTS

2010/0179130 A1  7/2010  Schneider et al.

FOREIGN PATENT DOCUMENTS

| KR | 10-2001-0071872 A | 7/2001 |
|---|---|---|
| KR | 10-1078376 B1 | 10/2011 |

OTHER PUBLICATIONS

PreventObesity, 2015, http://www.mayoclinic.org/diseases-conditions/obesity/basics/prevention/con-20014834.*
PreventDiabetes, 2015, http://www.diabetes.org/are-you-at-risk/.*
PreventDyslipidemia, 2015, http://www.diabetes.org/are-you-at-risk/.*
PreventFattyLiver, 2015, http://www.mayoclinic.org/diseases-conditions/nonalcoholic-fatty-liver-disease/basics/prevention/con-20027761.*
Reid et al., 2002, caplus an 2002:90009.*
Jaehne et al., 2007, caplus an 2007:585073.*
Yazawa et al., 2007, caplus an 2007:937376.*
International Search Report for PCT/KR2012/011548.

* cited by examiner

*Primary Examiner* — Sun Jae Yoo
(74) *Attorney, Agent, or Firm* — Harness, Dickey & Pierce, P.L.C.

(57) ABSTRACT

The present invention provides novel piperine derivatives. The present pharmaceutical or food composition containing a piperine derivative as an active ingredient is very effective in preventing or treating metabolic diseases including obesity, diabetes, dyslipidemia, fatty liver and insulin resistance syndrome. Piperine derivatives of the present invention useful as pharmaceuticals compositions or functional food compositions has therapeutic efficacies for metabolic syndrome selected from the group consisting of obesity, diabetes, hyperlipidemia, fatty liver and insulin resistance syndrome, and also suppress the differentiation of progenitor cells and reduce the accumulation of triglycerides.

9 Claims, 22 Drawing Sheets

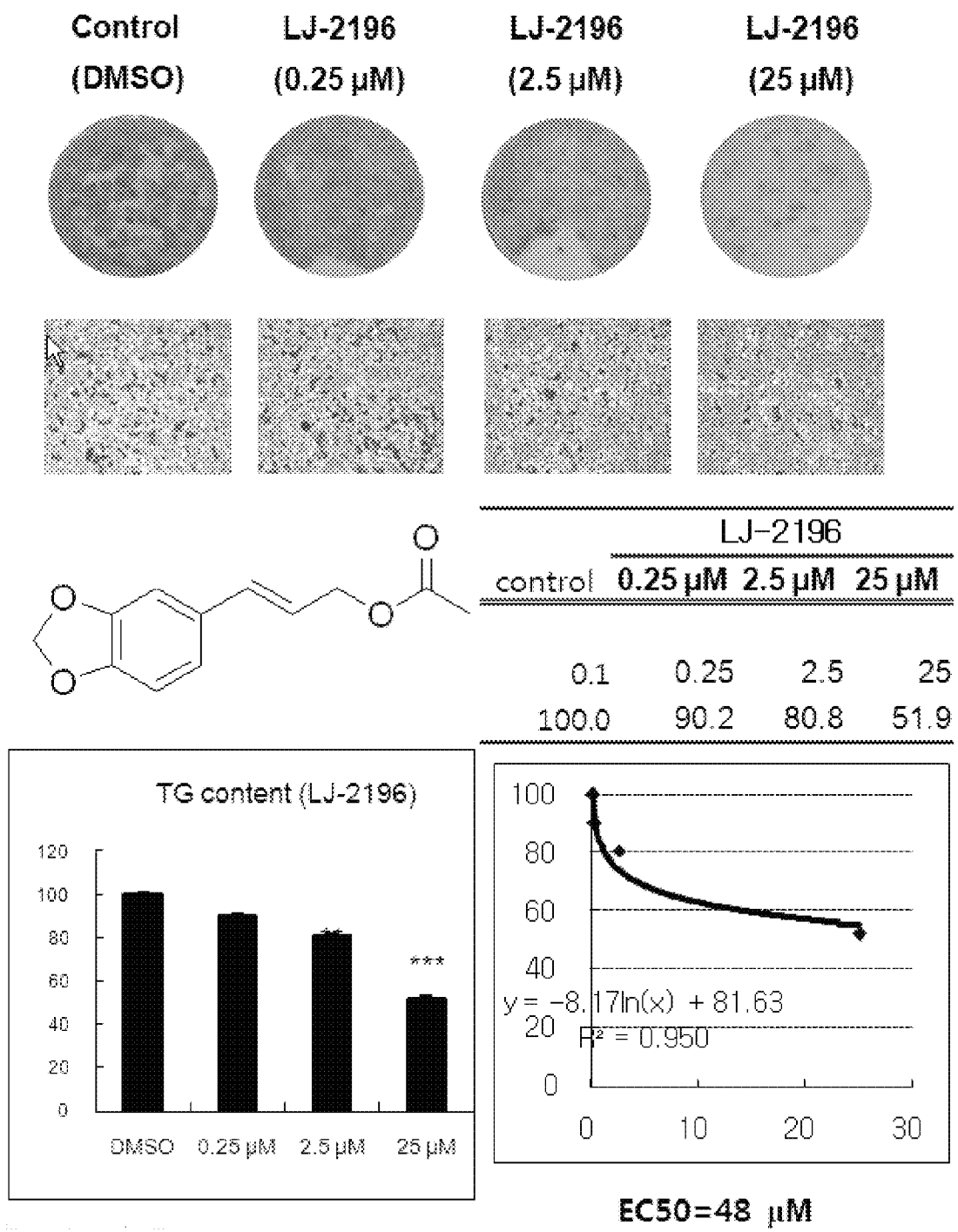

Fig. 1e
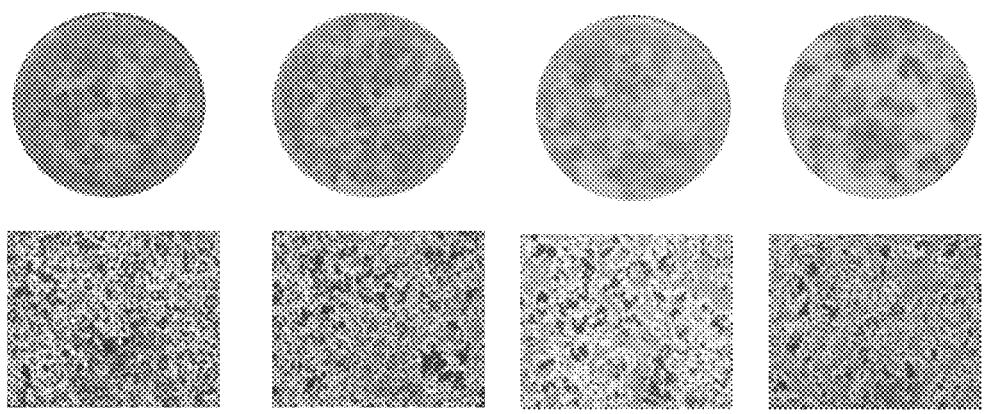
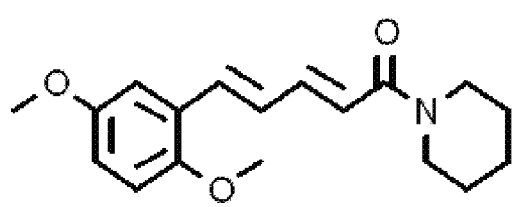
| | LJ-2488 | | |
|---|---|---|---|
| control | 0.25 μM | 2.5 μM | 25 μM |
| 0.1 | 0.25 | 2.5 | 25 |
| 100.0 | 82.8 | 77.1 | 73.1 |
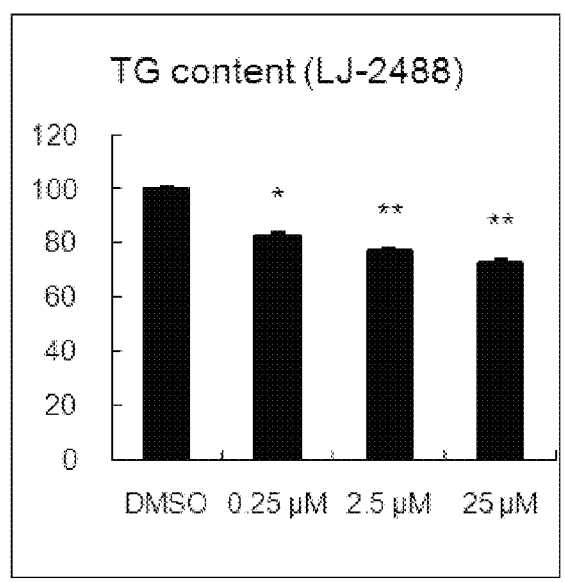
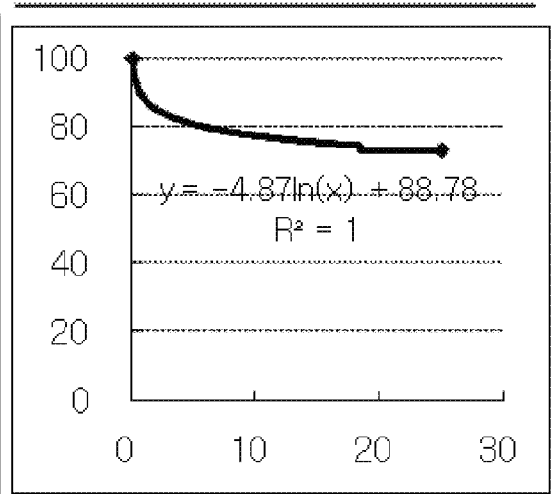
$y = -4.87\ln(x) + 88.78$
$R^2 = 1$
EC50 = 2.8 mM

Fig. 1g
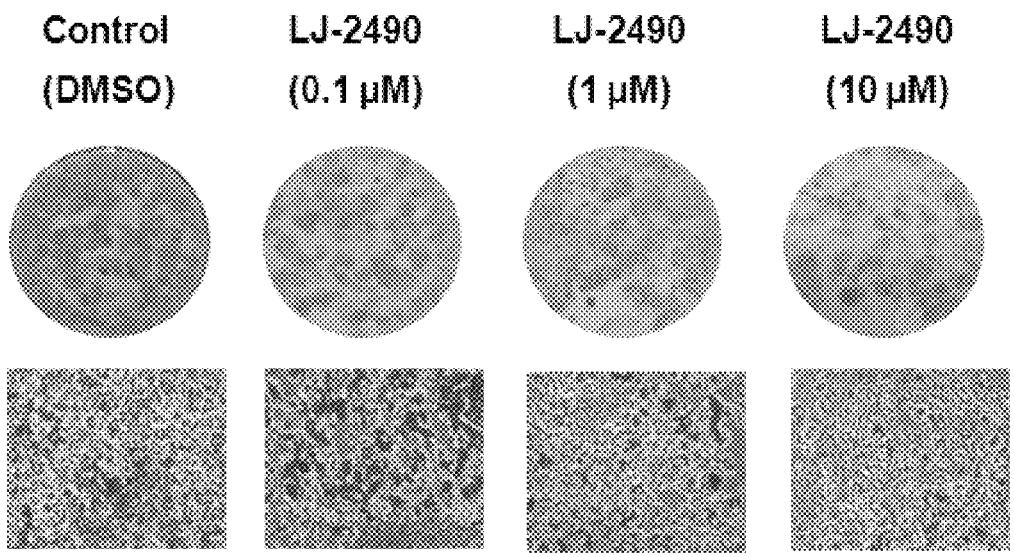
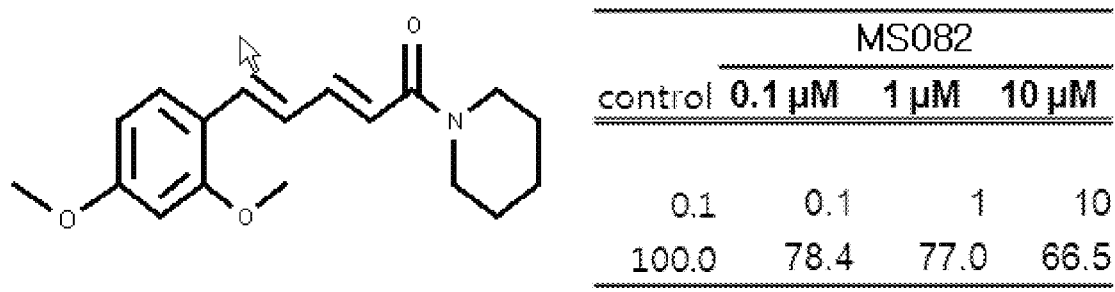
| | MS082 | | |
|---|---|---|---|
| control | 0.1 µM | 1 µM | 10 µM |
| 0.1 | 0.1 | 1 | 10 |
| 100.0 | 78.4 | 77.0 | 66.5 |
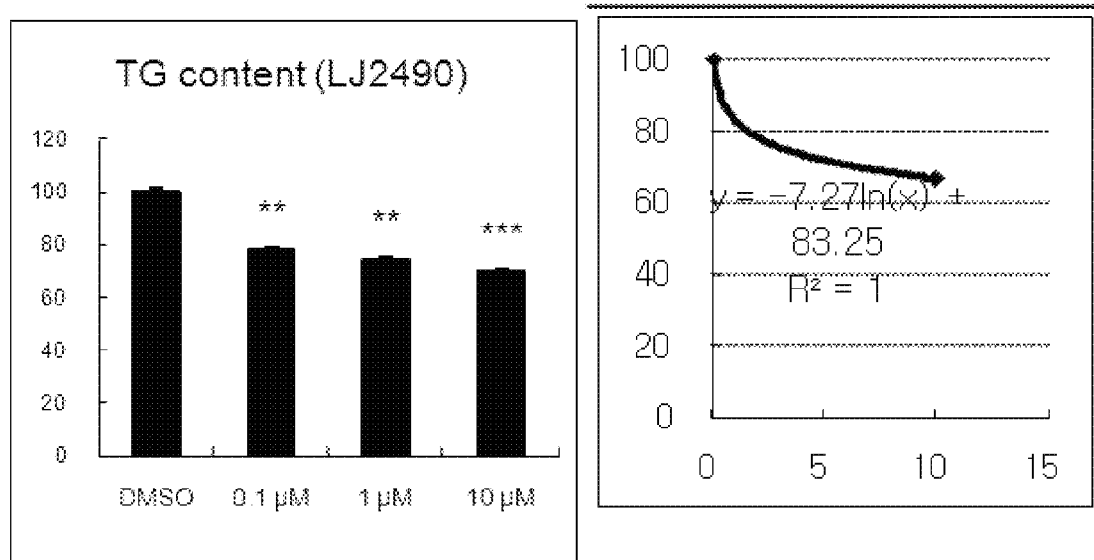
EC50=113 µM Fig. 1i
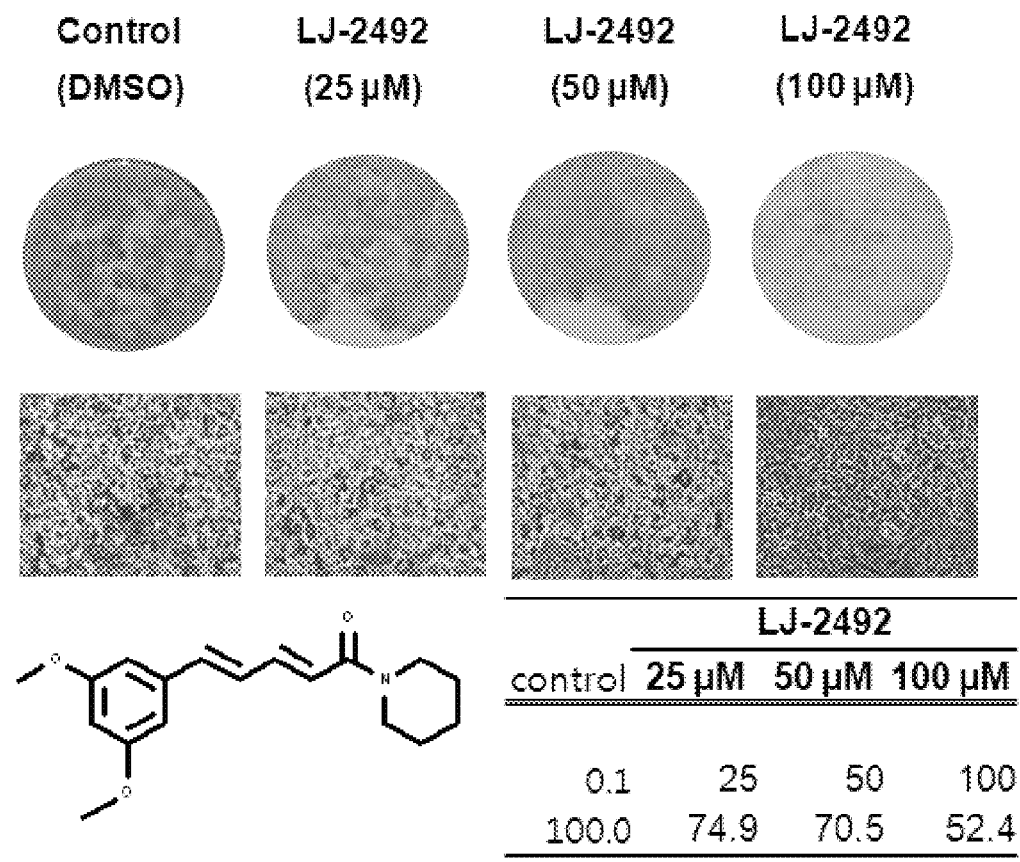
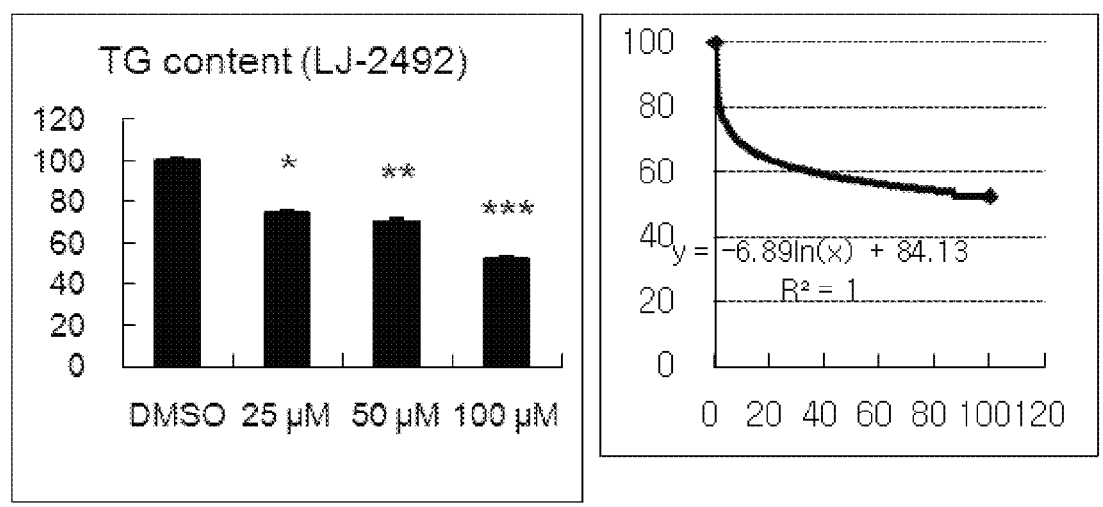
EC50=142 μM

EC50=196 µM

Fig. 1k
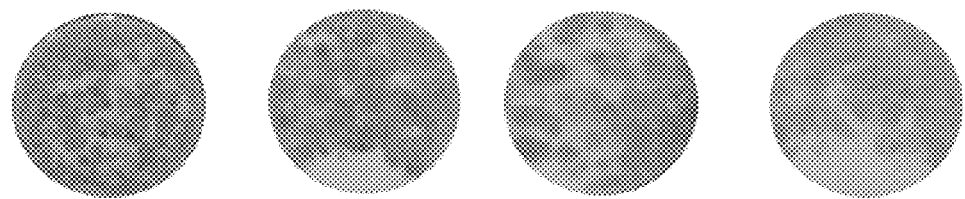
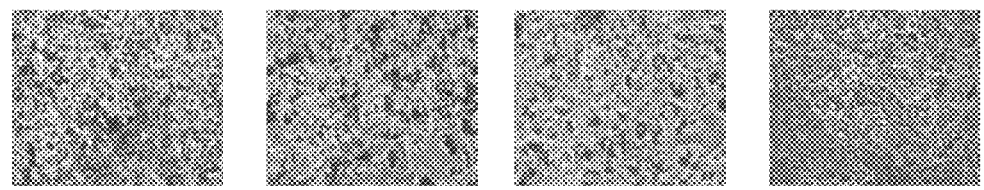
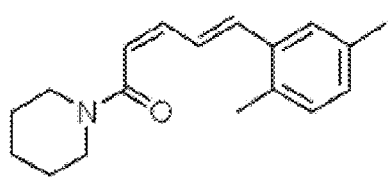
| | LJ-2498 | | |
|---|---|---|---|
| control | 10 μM | 25 μM | 50 μM |
| 0.1 | 10 | 25 | 50 |
| 100.0 | 68.8 | 59.8 | 55.7 |
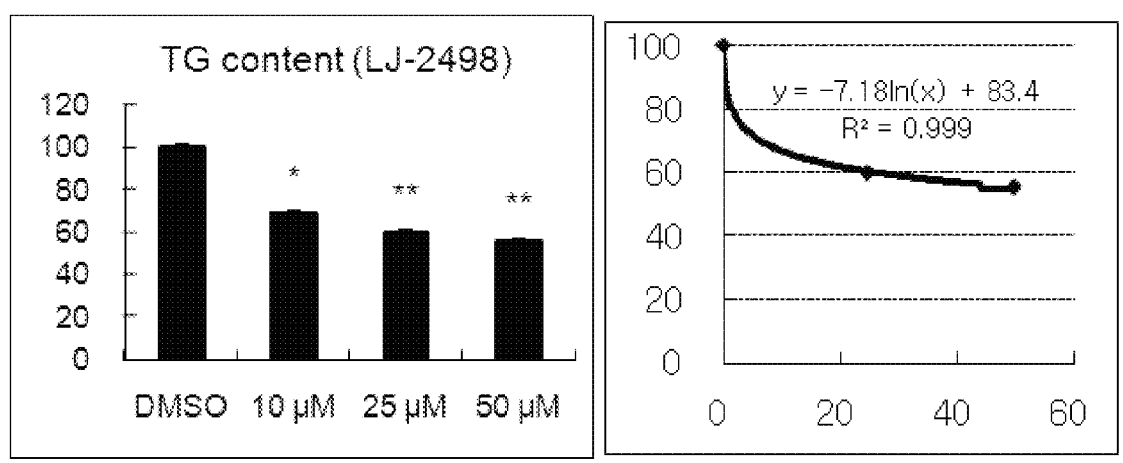
EC50=114 μM Fig. 3
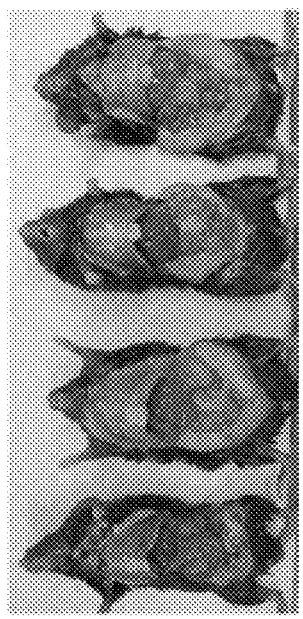
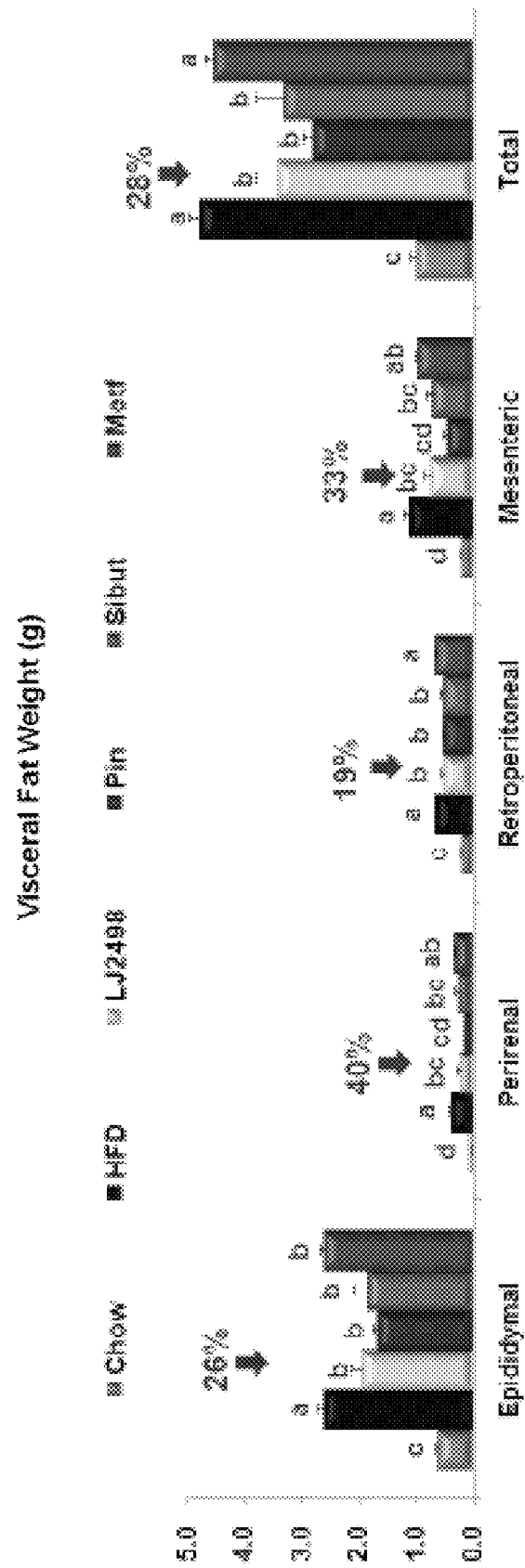

Fig. 6
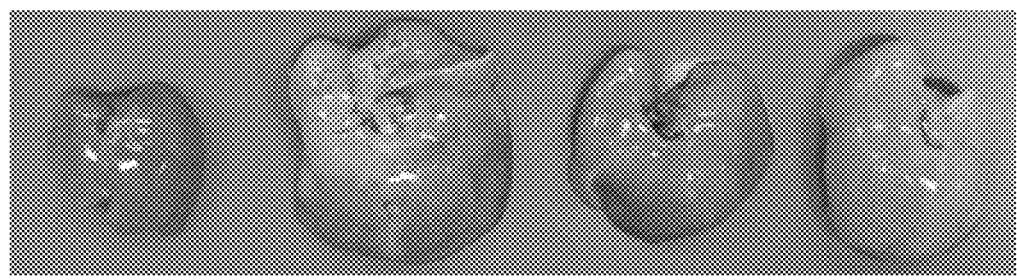
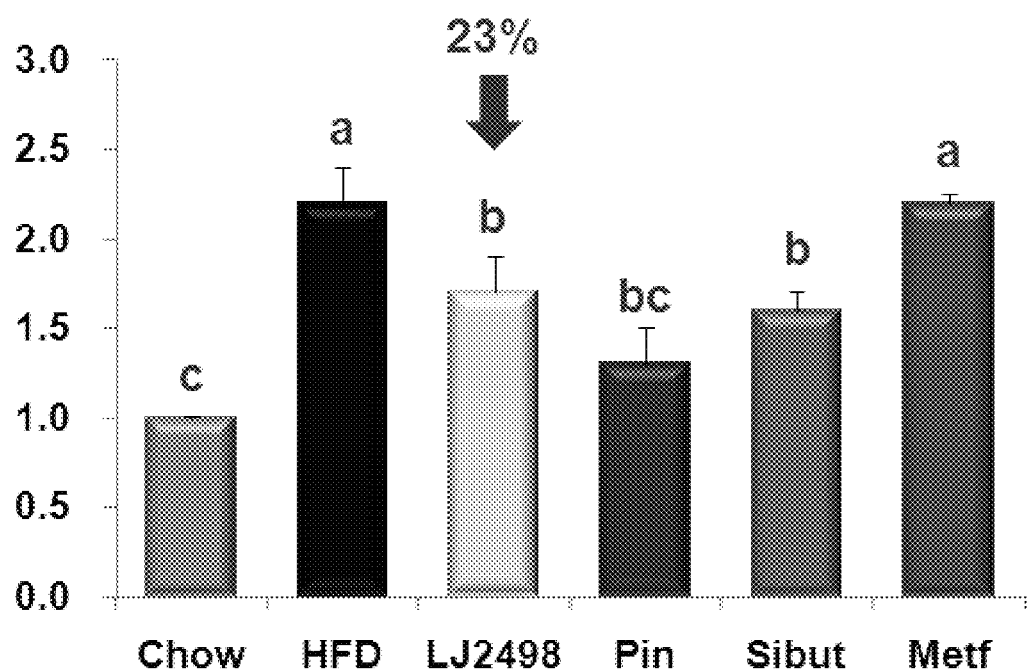

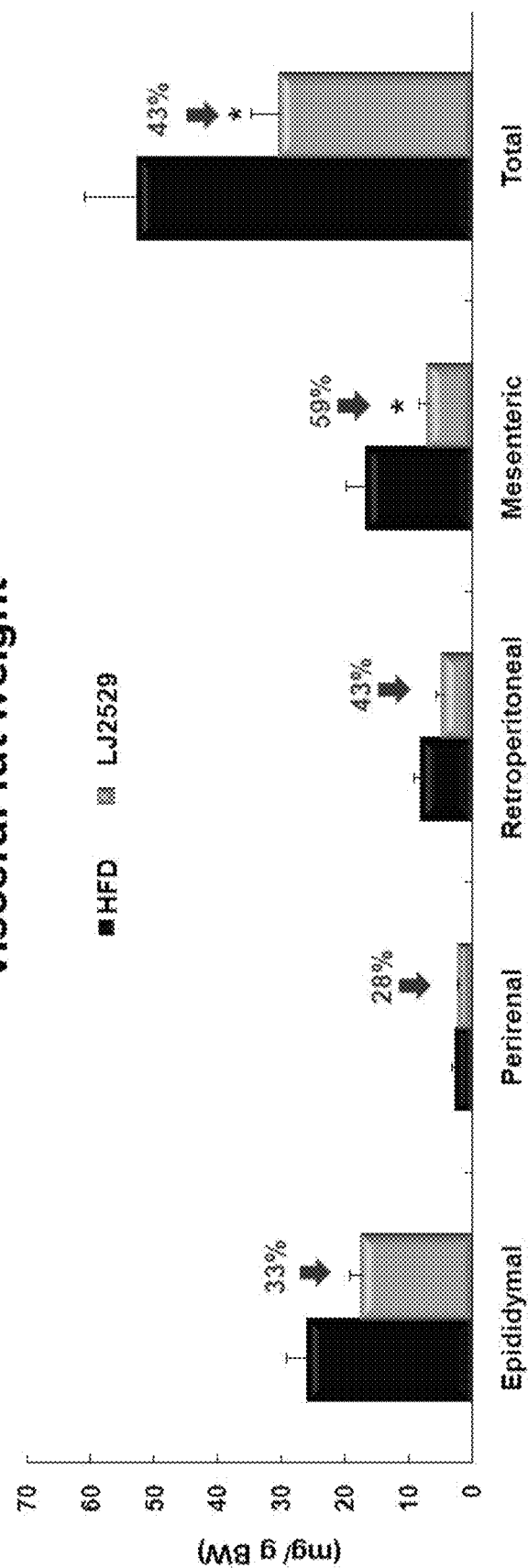

PIPERINE DERIVATIVES AND USES THEREOF

CROSS REFERENCE TO RELATED APPLICATIONS AND CLAIM OF PRIORITY

This patent application claims benefit under 35 U.S.C. 119(e), 120, 121, or 365(c), and is a National Stage entry from International Application No. PCT/KR2012/011548, filed Dec. 27, 2012, which claims priority to Korean Patent Application No. 10-2012-0009362, filed Jan. 31, 2012, entire contents of which are incorporated herein by reference.

BACKGROUND

1. Field of the Invention

The present invention relates to novel piperine derivatives and uses thereof.

2. Background of Technique

As abdominal obesity increases in modern people with the change in lifestyles, occurrence of metabolic syndromes including diabetes, hypertension, dyslipidemia, insulin resistance, etc. is increasing rapidly. These diseases increase the risk of incidence one another and are commonly related to the cause of metabolic changes, such as aging, stress and suppressed immune system. Obesity is considered unattractive and causes such chronic diseases as fatty liver, hypertension, diabetes, cardiovascular diseases, or the like. According to the 2007 Korea National Health and Nutrition Examination Survey recently reported by the Ministry of Health & Welfare, 31.7% of Korean adults turned out to be obese, meaning that 3 out of 10 Korean adults are exposed to obesity-related complications. The increase in overweight and obese population leads to increased prevalence of chronic diseases. The number of diabetic patients in Korea is expected to increase from 3,000,000 in 2007 to 5,450,000 in 2030, meaning that 10% of Koreans will be diabetic patients. In 2005, deaths caused by diabetes in Korea were 35.5 per 100,000 people, 3-7 times more than those of Japan (5.9), England (7.5) or Germany (16.6). According to the Korea Institute for Health and Social Affairs, the socioeconomic loss caused by obesity and obesity-related complications in 2006 is estimated at 2.1 trillion won including medical cost and indirect cost such as loss of earning. Thus, in 2010, the Korean government has decided to reduce the obesity rate down to 20% in adults and to 15% in youth, and is exploring ways to accurately define and diagnose obesity and metabolic diseases.

At present, 1.7 billion people amounting to about 25% of the world population are overweight (BMI>25) and more than 300 million people including 120 million in the US, Europe and Japan are classified as obese (BMI>30). Among the OECD countries, the US has the highest obesity rate of 31% of population, followed by Mexico (24%), England (23%), Greece (22%), Australia (22%), New Zealand (21%), Hungary (19%), Canada (14%), Spain (13%), Ireland (13%), Germany (13%), Portugal (13%), Finland (13%), Turkey (12%) and Belgium (12%). The number of obese people in China is 70 million and the body weight control-related market is expanding, estimated at about 10 billion yuan. Childhood obesity is also increasing rapidly worldwide, with 1 in 5 children being obese. As such, childhood obesity is becoming a serious social issue. Since childhood obesity is the main cause of the life style diseases including diabetes, hypertension, stroke, etc. with increased blood cholesterol and triglyceride level, 80% or more of obese children are likely to become obese adults. Further, since increased fat stimulates secretion of sex hormones and induces early adolescence, childhood obesity may cause growth problems. Also, it negatively affects blood circulation and nourishment.

Obesity drugs that are marketed inside and outside Korea include 'Xenical' (Roche Korea) with orlistat as main ingredient and approved by the FDA, 'Reductil' (Ilsung Pharmaceuticals) with sibutramine as main ingredient, 'Exolise' (Guju Pharma) with green tea catechol as main ingredient, or the like. Xenical, which reduces absorption of fat by inhibiting lipase, has the gastrointestinal-related side effects such as steatorrhea, gas generation and reduced absorption of oil-soluble vitamins. Reductil, which increases serotonin and noradrenaline levels in the sympathetic nervous system, has side effects such as headache, dry mouth, loss of appetite, insomnia, constipation, etc. Besides, a large number of anti-obesity drugs have been withdrawn from the market due to severe side effects. For example, aminophylline is reported to have various side effects in the nervous, circulatory and digestive systems despite its excellent effect of reducing body fat. Also, fenfluramine, dexfenfluramine, topiramate, ephedrine, etc. have been banned from being marketed as obesity drugs. As the synthetic drugs show limitations in side effects and in overcoming chronic diseases, foods and drugs derived from natural sources are drawing attentions.

Piperine is a compound found in long pepper, black pepper, cubeb, or dill, and its structural formula is $C_{17}H_{19}NO_3$. It has been so far reported that piperine has biological activities such as an antioxidant effect, an anti-mutagenic effect, and an anti-cancer effect, and serves to improve bioavailability of drugs such as resveratrol. The treatment of endothelial cells with piperine led to effective immune responses, such as increasing adhesion of neutrophils and leukocytes and suppressing migration of the p65 subunit of NK-kB from the cytoplasm to the nucleus. For Swiss albino mice, as a result of comparison between a group administered with of benzo[α] pyrene, which is carcinogen causing lung cancer, in an amount of 50 mg/kg body weight twice a week for 16 weeks and a group administered with piperine in an amount of 100 mg/kg body weight once a day for 4 weeks before administration of benzo[α]pyrene, the group pre-treated with piperine showed significantly high values of antioxidant indexes such as superoxide dismutase (SOD), catalase (CAT), glutathione peroxidase (GPX), reduced glutathione (GSH), vitamin E, vitamin C, or the like in the tissues. Thus, piperine was proven to have an antioxidant effect. Accordingly, piperine has been commercially used for products of various dietary supplements in a complex form, together with other plant extracts and phytochemicals, and has been on the market for the purpose of improving general health functions including an antioxidant function.

Throughout the specification, a number of publications and patent documents are referred to and cited. The disclosure of the cited publications and patent documents is incorporated herein by reference in its entirety to more clearly describe the state of the related art and the present disclosure.

SUMMARY

The inventors of the present disclosure have made efforts to develop chemicals having preventive or therapeutic activity for metabolic diseases including obesity, diabetes, dyslipidemia, fatty liver and insulin resistance syndrome. As a result, they have found out that novel piperine derivatives represented by Chemical Formula 1 or 2 have such activity.

The present disclosure is directed to providing novel piperine derivatives.

The present disclosure is also directed to providing a pharmaceutical composition for preventing or treating metabolic diseases including obesity, diabetes, dyslipidemia, fatty liver and insulin resistance syndrome, containing a piperine derivative as an active ingredient.

The present disclosure is also directed to providing a food composition for preventing or improving metabolic diseases including obesity, diabetes, dyslipidemia, fatty liver and insulin resistance syndrome, containing a piperine derivative as an active ingredient.

Other features and aspects will be apparent from the following detailed description, drawings, and claims.

BRIEF DESCRIPTION OF THE DRAWINGS

FIG. 3 shows visceral fat weight (g) and images of visceral fat tissues of mice fed with test diets (LJ-2498).

FIG. 6 represents liver weight (g) and images of liver tissues of mice fed with test diets (LJ-2498).

FIG. 9 shows visceral fat weight (g) of mice fed with test diets (LJ-2529).

DETAILED DESCRIPTION

Figure 1A:
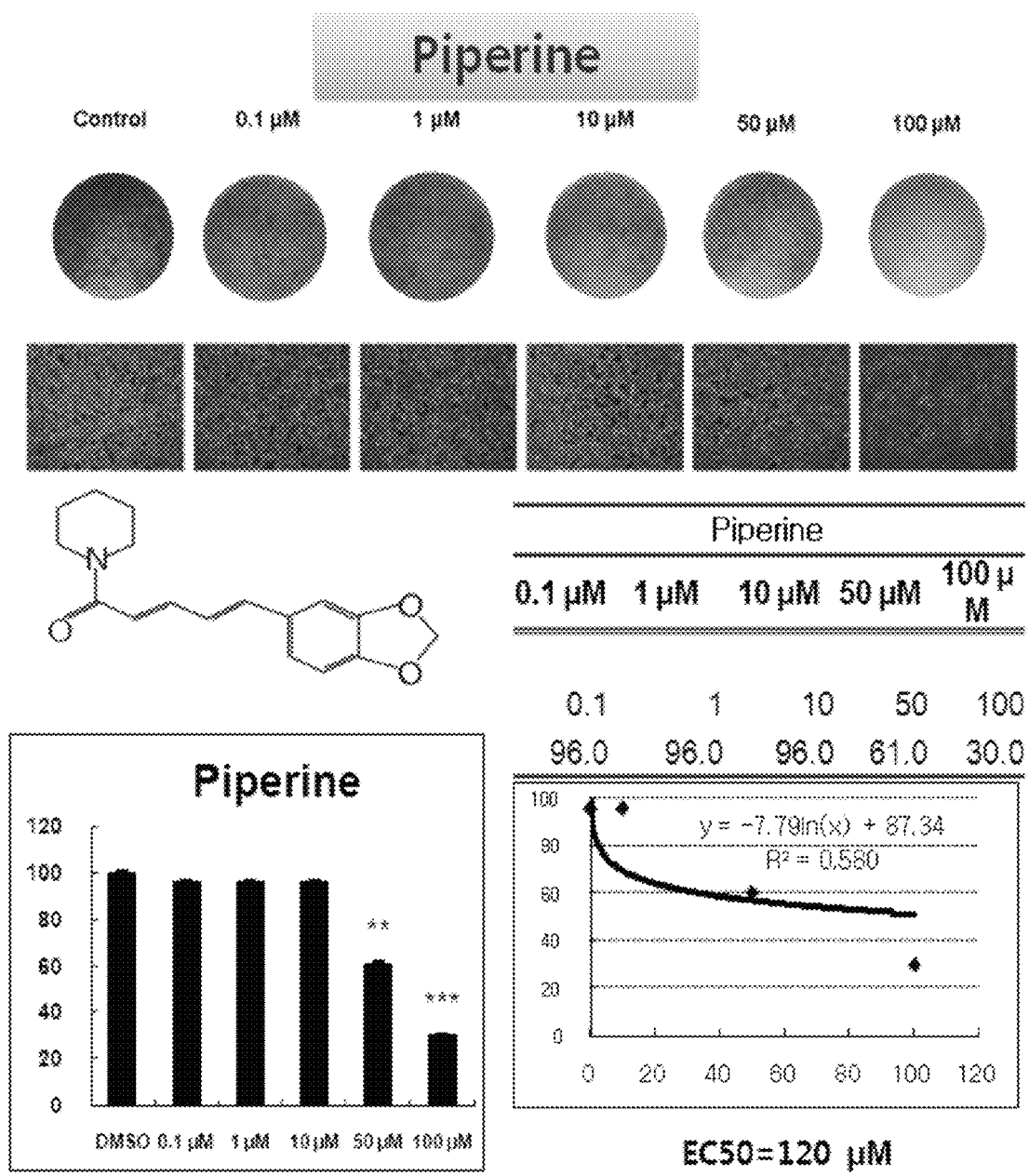
FIGS. 1a-1n represents preadipocyte differentiation inhibitory effects of piperine and piperine derivatives (LJ-2196, LJ-2477, LJ-2487, LJ-2488, LJ-2489, LJ-2490, LJ-2491, LJ-2492, LJ-2497, LJ-2498, LJ-2527, LJ-2529, SKKU-S-02).
Figure 1C:
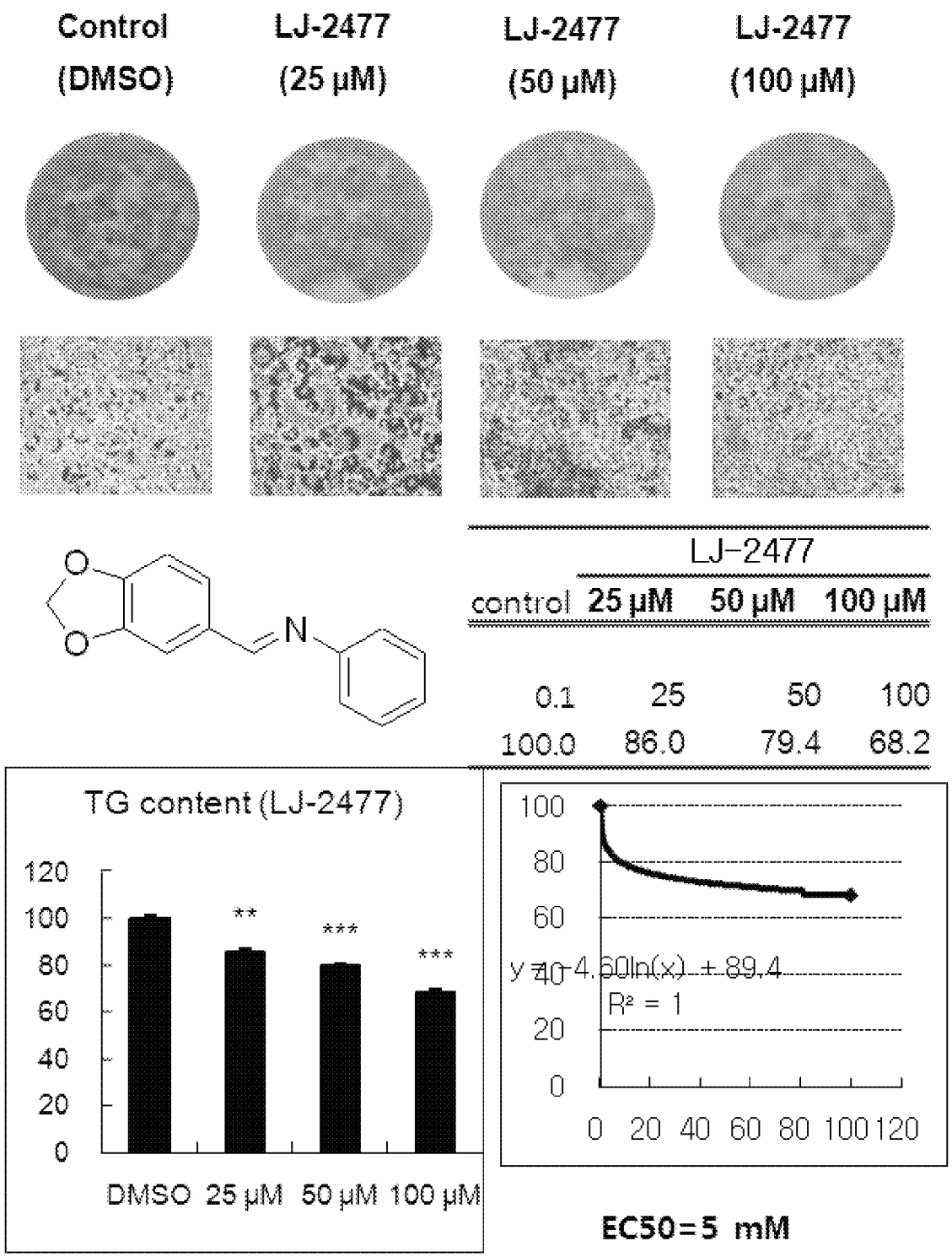
Figure 1D:
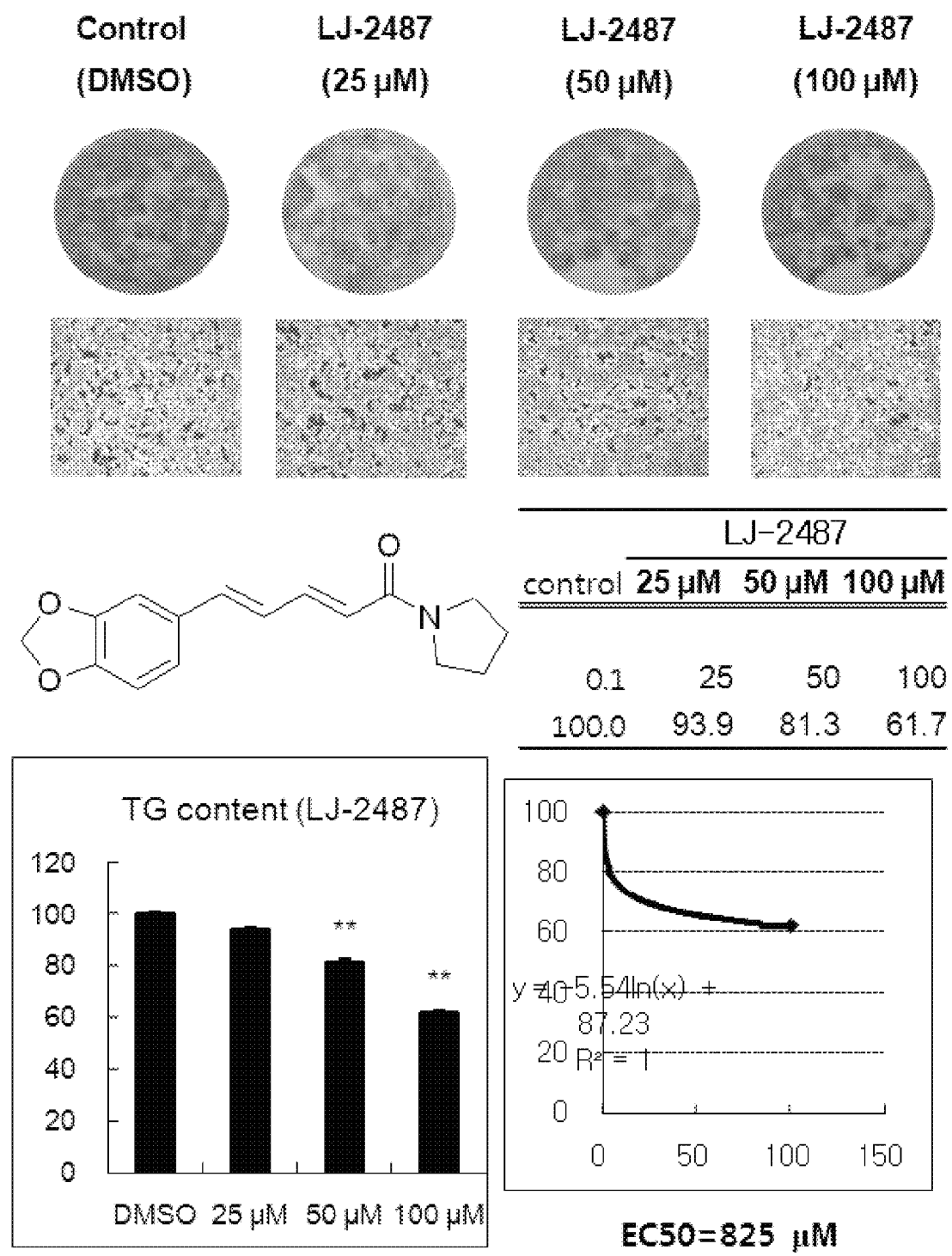
Figure 1F:
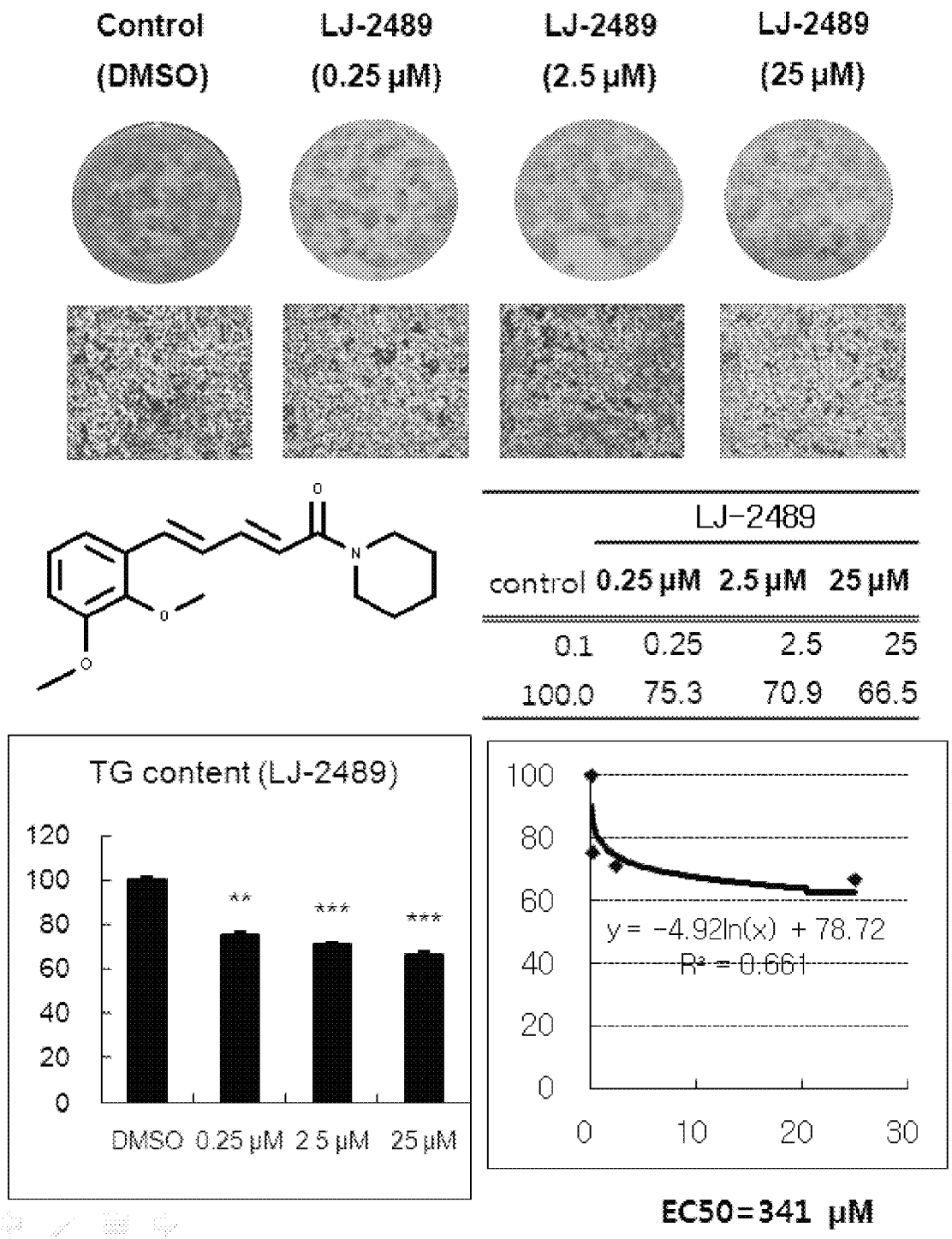
Figure 1H:
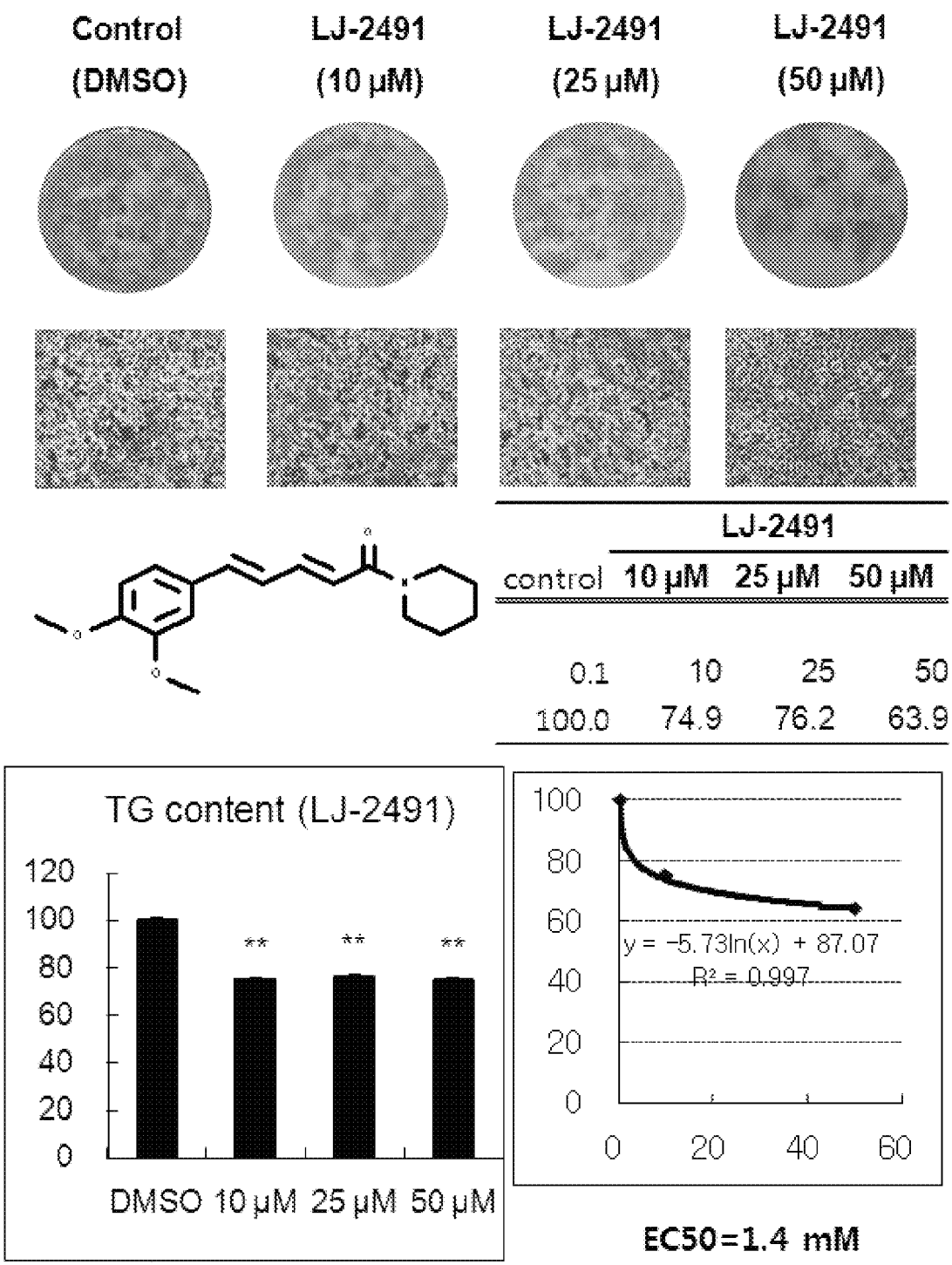
Figure 1J:
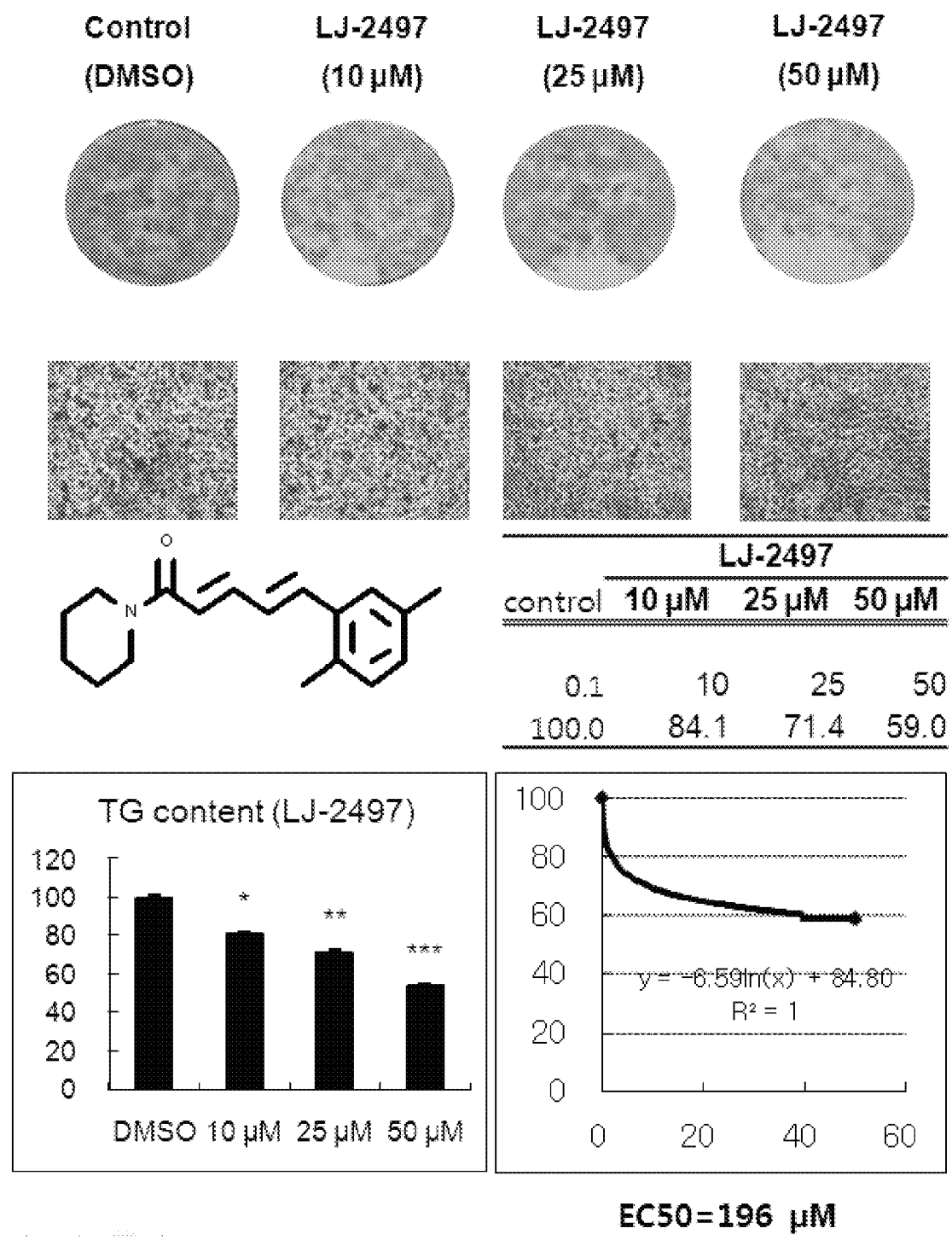
Figure 11:
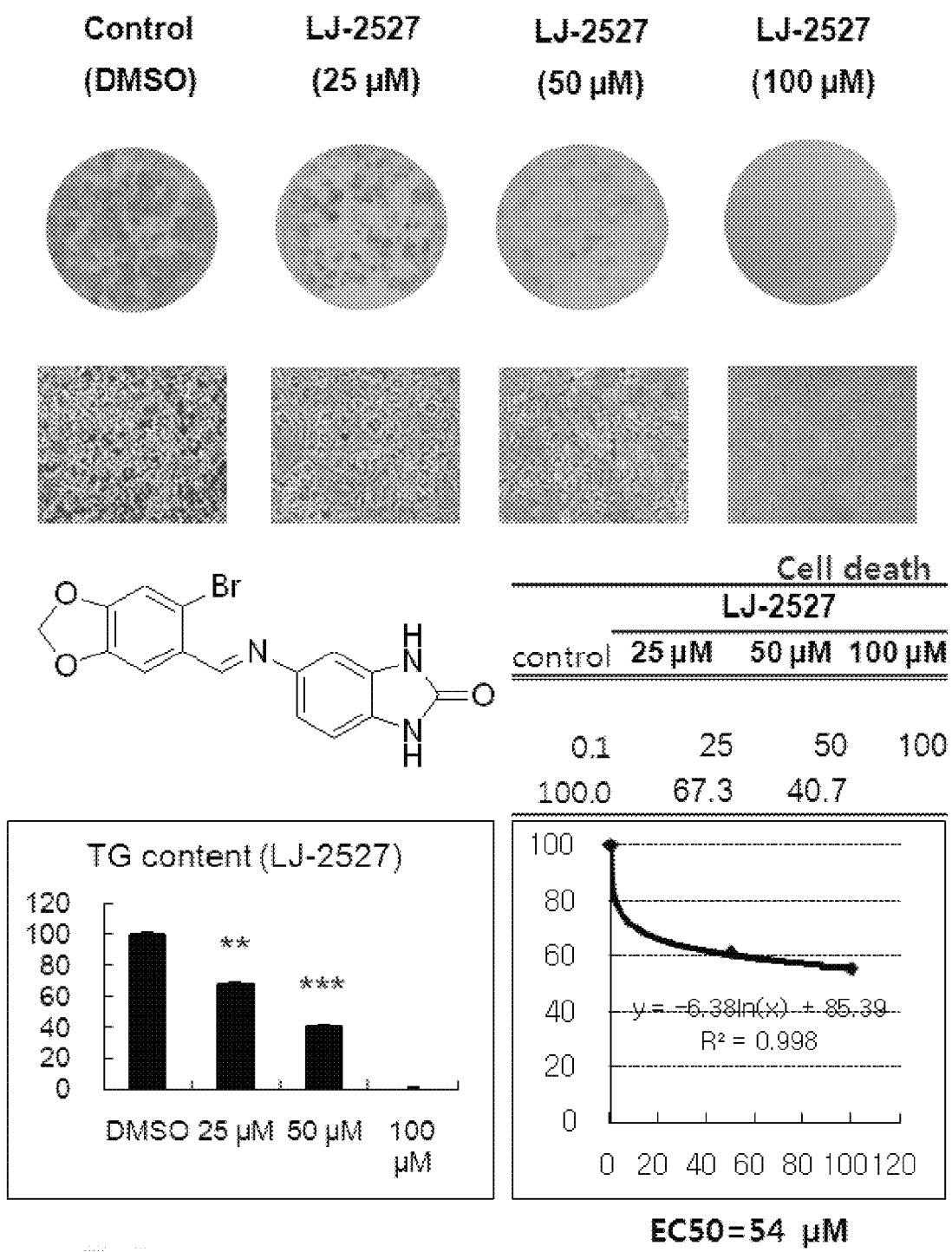
Figure 1M:
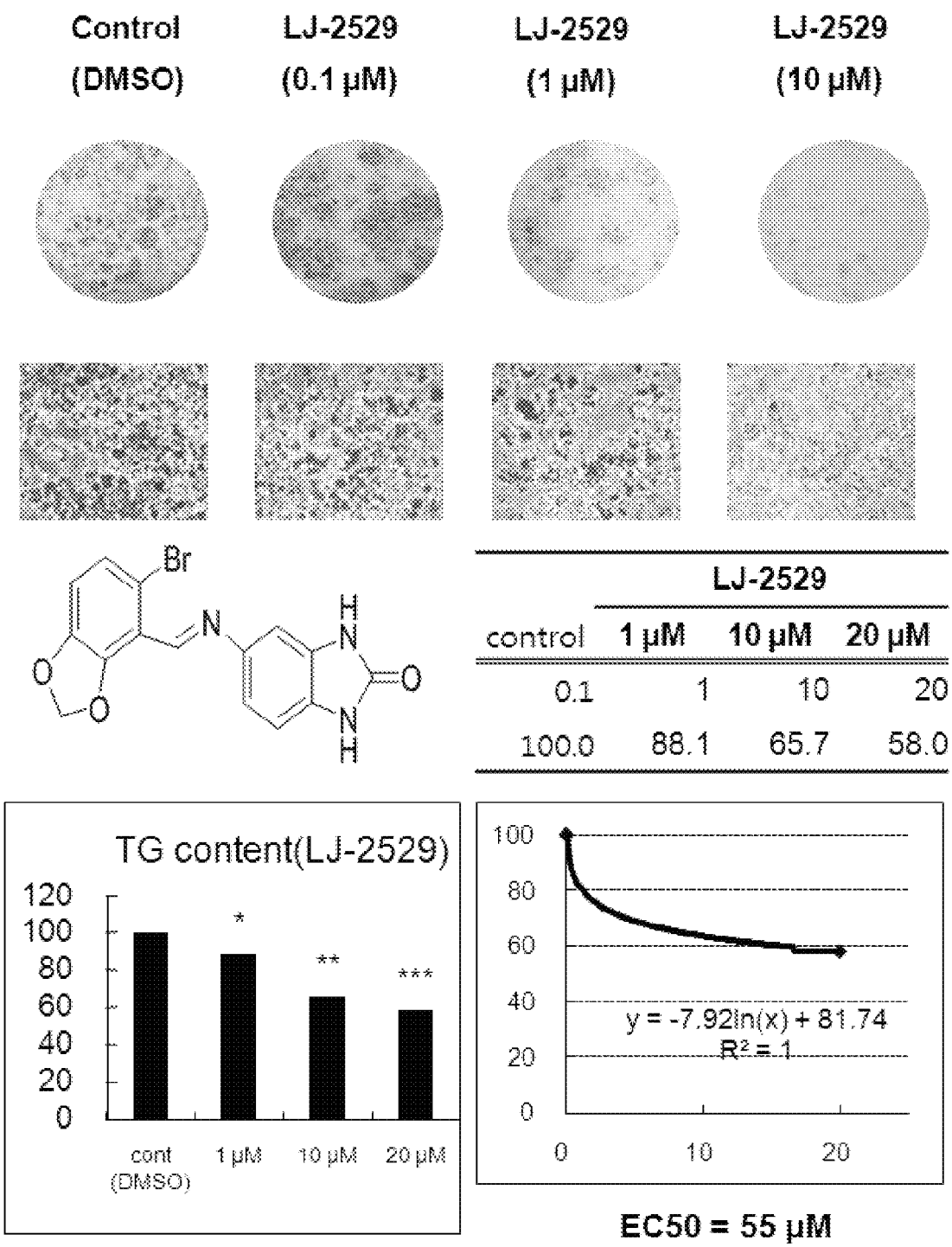

According to an aspect of the present invention, there is provided a piperine derivative represented by Chemical Formula 1 or Chemical Formula 2 below:

Chemical Formula 1

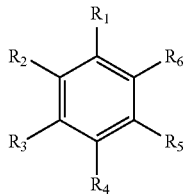

wherein, in Chemical Formula 1, $R_1$-$R_5$ are each independently hydrogen, $C_1$-$C_5$ alkyl or $C_1$-$C_5$ alkoxy; $R_2$ and $R_3$, when being linked to each other to form a ring structure, form a heterocyclic structure containing two oxygen atoms as heteroatoms; $R_6$ is

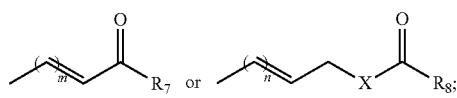

m is an integer of 1-4 and n is an integer of 1-4; $R_7$ is $C_1$-$C_5$ alkyl, pyrrolidine, or piperidine; X is oxygen or sulfur; $R_8$ is $C_1$-$C_5$ alkyl, pyrrolidine, or piperidine, and Chemical Formula 2

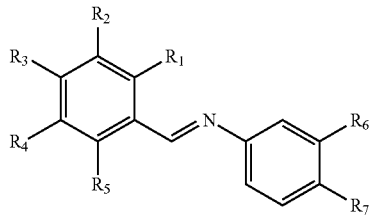

wherein, in Chemical Formula 2, $R_1$-$R_5$ are each independently hydrogen, $C_1$-$C_5$ alkyl, $C_1$-$C_5$ alkoxy, or halogen; $R_3$ and $R_4$, when being linked to each other to form a ring structure, form a heterocyclic structure containing two oxygen atoms as heteroatoms; $R_4$ and $R_5$, when being linked to each other to form a ring structure, form a heterocyclic structure containing two oxygen atoms as heteroatom; $R_6$ and $R_7$ are each independently hydrogen or $C_1$-$C_5$ alkyl; and $R_6$ and $R_7$, when being linked to each other to form a ring structure, form a heterocyclic structure containing two nitrogen atoms as heteroatoms.

The inventors of the present disclosure have made efforts to develop chemicals having preventive or therapeutic activity for metabolic diseases including obesity, diabetes, dyslipidemia, fatty liver and insulin resistance syndrome. As a result, they have found out that novel piperine derivatives have such activity.

According to the present invention, the piperine derivative represented by Chemical Formula 1 or 2 of the present invention inhibits the differentiation of preadipocytes in a dose-dependent manner (FIGS. 1b to 1n).

As used herein, the term "dyslipidemia" refers to abnormal lipid conditions, including hyperlipidemia, caused by aberrant lipoprotein metabolism as well as hypercholesterolemia, hypertriglyceridemia, and low HDL-cholesterolemia, due to increased levels of fat in the blood.

As used herein, the term "fatty liver" refers to a condition where fat accumulates excessively in liver cells due to the disorder of lipid metabolism. It may cause various diseases such as angina, myocardial infarction, stroke, arteriosclerosis and pancreatitis.

As used herein, the term "diabetes" refers to a chronic disease characterized by relative or absolute lack of insulin, leading to glucose intolerance. The term diabetes includes all kinds of diabetes, such as type 1 diabetes, type 2 diabetes and genetic diabetes. Type 1 diabetes, which is insulin-dependent diabetes, mainly results from the destruction of β-cells. Type 2 diabetes, which is non-insulin-dependent diabetes, is caused by insufficient secretion of insulin after meals or insulin resistance.

As used herein, the term "insulin resistance" refers to a physiological condition where insulin becomes less effective at lowering blood sugars and glucose is not effectively combusted by cells. Under high insulin resistance, the body may produce too much insulin, leading to hypertension or dyslipidemia as well as heart disease, diabetes, or the like. Especially, in type 2 diabetes, muscle and adipose tissues do not notice the increase of insulin.

As used herein, the term "insulin resistance syndrome" refers to a combination of disorders caused by insulin resistance, characterized by resistance of cells against the action of insulin, hyperinsulinemia, increase of very-low-density lipoprotein (VLDL) and triglyceride, decrease of high-density lipoprotein (HDL), hypertension, or the like. It is recognized as a risk factor for cardiovascular diseases and type 2 diabetes (Reaven G M., Diabetes, 37: 1595-607 (1988)). Also, insulin resistance is known to increase oxidative stress and change the signal transduction system in cells along with other risk factors such as hypertension, diabetes, smoking, etc., thus inducing inflammatory responses and leading to atherosclerosis (Freeman B A et al., Lab. Invest. 47: 412-26 (1982), Kawamura M et al., J. Clin. Invest. 94: 771-8 (1994)).

As used herein, the term "metabolic disease" refers to a group of diseases involving disorders of metabolism which are risk factors of various cardiovascular diseases and type 2 diabetes. It includes insulin resistance and complex and diverse metabolic disorders related thereto. In 1988, Reaven proposed insulin resistance as the factor underlying these disorders and named the constellation of abnormalities insulin resistance syndrome. However, in 1998, the World Health Organization (WHO) introduced the term metabolic syndrome or metabolic disease since all the aspects of the symptoms cannot be explained by insulin resistance.

The composition of the present disclosure comprising a piperine derivative as an active ingredient has activities of improving various metabolic diseases, e.g., obesity, diabetes, hyperlipemia, non-alcoholic fatty liver or insulin resistance syndrome. The composition of the present disclosure can prevent or treat metabolic diseases with various activities.

As used herein the term "hyperlipidemia" refers to a disease caused by higher level of blood lipids due to poor metabolism of lipids such as triglyceride and cholesterol. More specifically, hyperlipidemia is characterized by increased levels of lipids such as triglyceride, LDL cholesterol, phospholipids and free fatty acids in blood, including hypercholesterolemia and hypertriglyceridemia.

According to a preferred embodiment, the insulin resistance syndrome treated by the present invention comprises obesity, hypertension, atherosclerosis, hyperlipidemia, hyperinsulinemia, non-alcoholic fatty liver and type 2 diabetes.

According to a preferred embodiment, the composition of the present invention decreases levels of blood fat, liver fat or visceral fat.

The term "liver" or "visceral" is used to encompass organ, tissue and cell.

According to the present invention, a group fed with a diet containing the piperine derivative of the present invention significantly reduced body weight gain (FIGS. 2 and 8) and the lipid concentration in the blood (FIG. 4) and liver tissue (FIG. 7), and significantly reduced the total visceral fat weight (FIGS. 3 and 9).

According to a more preferred embodiment, the fat reduced by the present invention comprises triglyceride, cholesterol and free fatty acid.

According to a more preferred embodiment, the visceral fat reduced by the present invention comprises epididymal fat, perirenal fat, mesenteric fat and/or retroperitoneal fat.

According to a preferred embodiment, the composition of the present invention decreases activity of ALT (alanine aminotransferase) or AST (aspartate aminotransferase).

ALT and AST as indicators for liver function are enzymes exhibiting increased levels in blood upon damage of liver.

The composition of the present invention significantly reduced both ALT (by 27%) and AST (by 65%) in the blood as compared to HFD-fed groups, addressing that piperine derivatives have the excellent efficacies of improving fatty liver, preferably non-alcoholic fatty liver.

As used herein, the term "alkyl" refers to a saturated, substituted or unsubstituted hydrocarbon radical, which may be straight, branched or cyclic. For example, it includes methyl, ethyl, propyl, isobutyl, pentyl, hexyl, heptyl, octyl, nonyl, decyl, undecyl, tridecyl, pentadecyl, heptadecyl, etc. $C_1$-$C_5$ alkyl means an alkyl group having an alkyl unit of 1-5 carbon atoms. When the $C_1$-$C_5$ alkyl is substituted, the number of carbons in the substituent is not included. $R_1$-$R_5$ alkyl in Chemical Formula 1 may be preferably $C_{1-5}$ alkyl, more preferably $C_{1-4}$ alkyl, still more preferably $C_{1-3}$ alkyl, and most preferably $C_{1-2}$ alkyl. $R_1$-$R_5$ alkyl in Chemical Formula 2 may be preferably $C_{1-5}$ alkyl, more preferably $C_{1-4}$ alkyl, still more preferably $C_{1-3}$ alkyl, and most preferably $C_{1-2}$ alkyl.

As used herein, the term "alkoxy" refers to a radical formed as hydrogen is removed from an alcohol group. $R_1$-$R_5$ alkoxy in Chemical Formula 1 may be preferably $C_{1-5}$ alkoxy, more preferably $C_{1-4}$ alkoxy, still more preferably $C_{1-3}$ alkoxy, and most preferably $C_{1-2}$ alkoxy. $R_1$-$R_5$ alkoxy in Chemical Formula 2 may be preferably $C_{1-5}$ alkoxy, more preferably $C_{1-4}$ alkoxy, still more preferably $C_{1-3}$ alkoxy, and most preferably $C_{1-2}$ alkoxy.

As used herein, the term "halogen" refers to a halogen element. For example, it includes fluoro, chloro, bromo and iodo.

As used herein, the term "heterocyclic structure containing an oxygen atom as a heteroatom" refers to a non-aromatic cyclic hydrocarbon group which contains carbon, hydrogen, and at least one heteroatom (oxygen). The number of the heteroatoms may be preferably 1-4, more preferably 1-3, still more preferably 1-2, and most preferably 2. In Chemical Formula 1, $R_2$ and $R_3$ are linked to each other to form a ring structure. The ring structure forms a heterocyclic structure containing two oxygen atoms as heteroatoms, and the heterocyclic structure is preferably dioxolane.

In Chemical Formula 2, $R_3$ and $R_4$ or $R_4$ and $R_5$ are linked to each other to form a ring structure. The ring structure forms a heterocyclic structure containing two oxygen atoms as heteroatoms, and the heterocyclic structure is preferably dioxolane.

In Chemical Formula 1, $R_6$ is

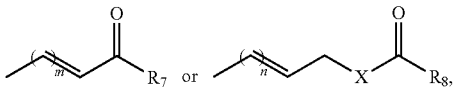

In $R_6$, m is an integer of 1-4, preferably 1-3, and more preferably 1-2. In $R_6$, n is an integer of 1-4, preferably 1-3, and more preferably 1-2. In $R_6$, X is oxygen or sulfur.

As used herein, the term "pyrrolidone" refers to a heterocyclic structure containing four carbon atoms and one nitrogen atom, and its chemical formula is $C_4H_9N$.

As used herein, the term "piperidine" refers to a heterocyclic structure containing five methylene units and one nitrogen atom, and its chemical formula is $(CH_2)_5NH$.

As used herein, the term "heterocyclic structure containing a nitrogen atom as a heteroatom" refers to a non-aromatic cyclic hydrocarbon group which contains carbon, hydrogen, and at least one heteroatom (nitrogen). The number of the heteroatoms may be preferably 1-4, more preferably 1-3, still more preferably 1-2, and most preferably 2. In Chemical Formula 2, $R_6$ and $R_2$ are linked to each other to form a ring structure. The ring structure forms a heterocyclic structure containing two nitrogen atoms as heteroatoms, and the heterocyclic structure is preferably imidazolone or imidazolethione.

In an exemplary embodiment of the present disclosure, the piperine derivative is a compound selected from the group consisting of compounds represented by Chemical Formulas 3-15 below:

Chemical Formula 3

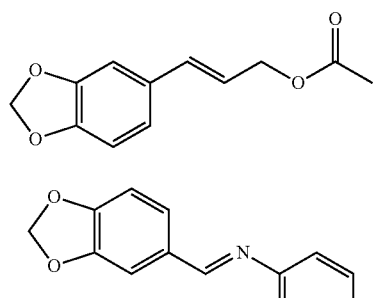

Chemical Formula 4

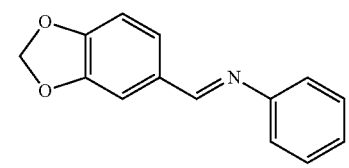 [SMILES: C(=N\c1ccccc1)/c1ccc2c(c1)OCO2]

Chemical Formula 5

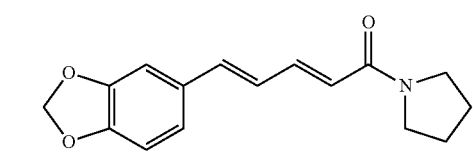 [SMILES: O=C(/C=C/C=C/c1ccc2c(c1)OCO2)N1CCCC1]

Chemical Formula 6

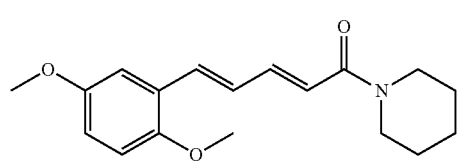 [SMILES: COc1ccc(OC)c(/C=C/C=C/C(=O)N2CCCCC2)c1]

Chemical Formula 7

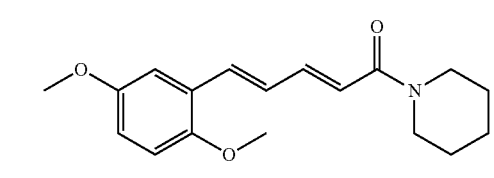

Chemical Formula 8

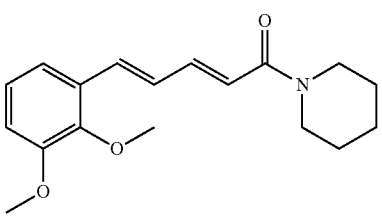

Chemical Formula 9

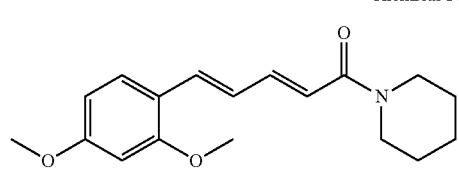

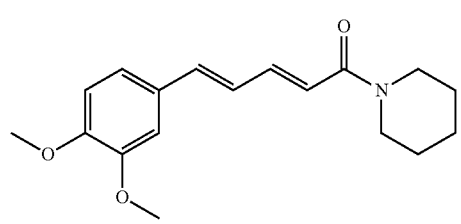

Chemical Formula 10

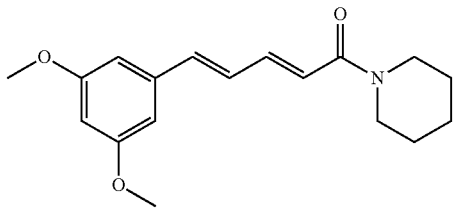

Chemical Formula 11

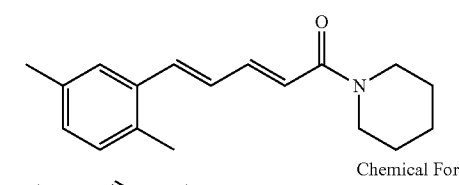

Chemical Formula 12

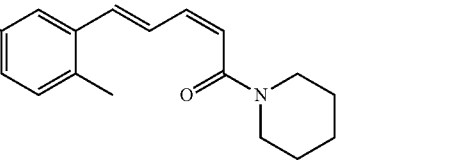

Chemical Formula 13

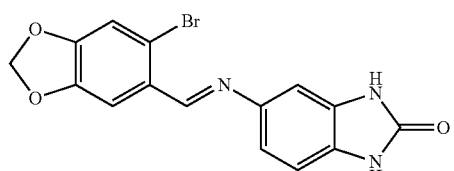

Chemical Formula 14

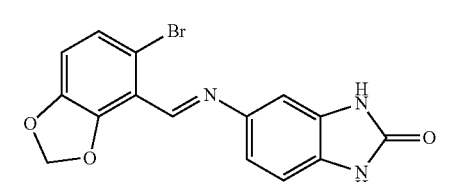

Chemical Formula 15

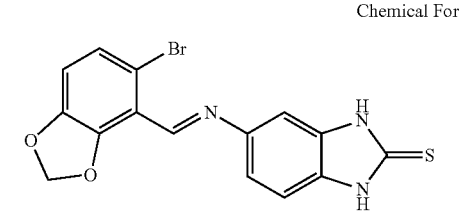

When the composition of the present disclosure is prepared as a pharmaceutical composition, the pharmaceutical composition of the present disclosure may comprise a pharmaceutically acceptable carrier. The pharmaceutically acceptable carrier included in the pharmaceutical composition of the present disclosure is one commonly used in the preparation of formulations and includes lactose, dextrose, sucrose, sorbitol, mannitol, starch, gum acacia, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, mineral oil, etc., but is not limited thereto. The pharmaceutical composition of the present disclosure may further include, in addition to the above-described components, a lubricant, a wetting agent, a sweetener, a fragrance, an emulsifier, a suspending agent, a preservative, or the like. Suitable pharmaceutically acceptable excipients and formulations are described in detail in Remington's Pharmaceutical Sciences (19th ed., 1995).

The pharmaceutical composition of the present disclosure may be administered orally or parenterally. The parenteral administration may include intravenous, subcutaneous, intramuscular, intraperitoneal, transdermal injections, and the like.

An appropriate administration dosage of the pharmaceutical composition of the present disclosure may be determined variously depending on such factors as preparation method, administration method, age, body weight and gender of a patient, pathological condition, diet, administration time, administration route, excretion rate or response sensitivity. Specifically, a daily dosage of the pharmaceutical composition of the present disclosure may be 0.001-100 mg/kg.

The pharmaceutical composition of the present disclosure may be prepared into a unit dosage form or multiple dosage form along with a pharmaceutically acceptable carrier and/or excipient according to a method that can be easily employed by those skilled in the art. The formulation may be in the form of solution in oily or aqueous medium, suspension, syrup, emulsion, extract, dust, powder, granule, tablet or capsule, and may further include a dispersant or stabilizer.

When the composition of the present disclosure is prepared as a food composition, the food composition of the present disclosure may comprise, in addition to piperine derivatives of the present disclosure as the active ingredient, ingredients commonly added for preparation of food. Since the piperine derivatives of present invention are described above, the common descriptions between them are omitted in order to avoid undue redundancy leading to the complexity of this specification. For example, proteins, carbohydrates, fats, nutrients, seasoning or flavors may be added. The carbohydrate may be, for example, a sugar such as a monosaccharide, e.g. glucose, fructose, etc., a disaccharide, e.g. maltose, sucrose, oligosaccharide, etc. or a polysaccharide, e.g. dextrin, cyclodextrin, etc. or a sugar alcohol such as xylitol, sorbitol, erythritol, etc. The flavor may be a natural flavor [thaumatin, stevia extract (e.g. rebaudioside A, glycyrrhizin, etc.]) or a synthetic flavor (saccharin, aspartame, etc.).

For example, when the food composition of the present disclosure is prepared as a drink, it may further comprise, in addition to piperine derivatives of the present disclosure as the active ingredient, citric acid, high-fructose corn syrup, sugar, glucose, acetic acid, malic acid, fruit juice, eucommia extract, jujube extract, licorice extract, or the like.

The features and advantages of the present invention may be summarized as follows:

(a) The present invention provides novel piperine derivatives.

(b) The present pharmaceutical or food composition containing a piperine derivative as an active ingredient is very effective in preventing or treating metabolic diseases including obesity, diabetes, dyslipidemia, fatty liver and insulin resistance syndrome.

(c) Piperine derivatives of the present invention useful as pharmaceuticals compositions or functional food compositions has preventive or therapeutic activity for metabolic syndrome selected from the group consisting of obesity, diabetes, hyperlipidemia, fatty liver and insulin resistance syndrome, and also suppress the differentiation of progenitor cells and reduce the accumulation of triglycerides.

The examples and experiments will now be described. The following examples and experiments are for illustrative purposes only and not intended to limit the scope of the present disclosure.

Example 1

Synthesis and Structure of Novel Piperine-Based Compound

Synthesis of (2E,4E)-5-(benzo[d][1,3]dioxol-5-yl)penta-2,4-dienoic acid

Piperine (200 mg, 0.70 mmol) dissolved in anhydrous ethanol and KOH (1.18 g, 21.0 mmol) were mixed and heated to reflux for 12 hours. Upon completion of the experiment, the pH value of the reaction mixture solution was adjusted to 2-3 using hydrochloric acid. After the ethanol was distilled under reduced pressure, the residue was diluted with EtOAC (30 mL) and washed with a saturated solution of NaCl, followed by drying over anhydrous $Na_2SO_4$. The solvent was distilled under reduced pressure to give a target compound (121 mg, yield: 79.1%).

1H NMR (500 MHz, Acetone) d 7.37-7.42 (ddd, 1H, J=5.1 Hz), 7.17 (d, 1H, J=1.8 Hz), 7.03 (dd, 1H, J=1.8 Hz), 6.96 (dd, 1H, J=1.4 Hz), 6.85 (d, 1H, J=7.8 Hz), 6.04 (s, 2H), 5.96-5.99 (d, 2H, J=15.2 Hz).

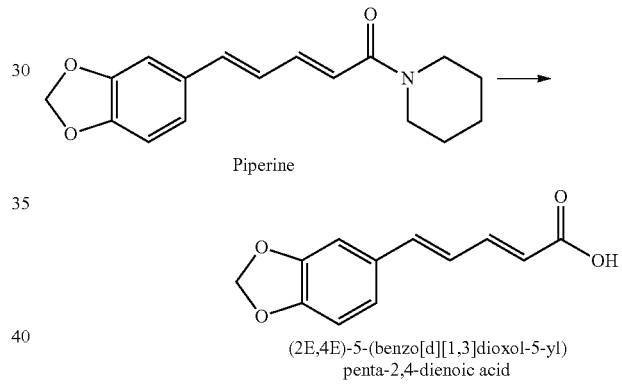

Synthesis of (2E,4E)-5-(benzo[d][1,3]dioxol-5-yl)-1-(pyrrolidin-1-yl)penta-2,4-diene-1-one (LJ-2487)

(2E,4E)-5-(benzo[d][1,3]dioxol-5-yl)penta-2,4-dienoic acid (50 mg, 0.23 mmol) was dissolved in 1,1'-carbonyldiimidazole (56 mg, 0.34 mmol) in THF (1.5 mL), followed by stirring for 1 hour. Then, pyrrolidone (0.03 mL, 0.34 mmol) was added thereto, followed by stirring for 6 hours. Upon completion of the reaction, the experiment was completely terminated by addition of distilled water. EtOAc was added to the reaction product to separate an oil layer and a water layer from each other, followed by washing with a saturated solution of NaCl and then drying over anhydrous $Na_2SO_4$. The solvent was distilled under reduced pressure. The residue was purified by column chromatography using hexane/ethyl acetate (1/1) to give a target compound (36.1 mg, yield: 58.1%).

1H NMR (500 MHz, $CDCl_3$) d 7.61-7.66 (m, 1H), 6.98 (d, 1H, J=1.9 Hz), 6.90 (dd, 1H, J=1.4 Hz), 6.84-6.87 (bs, 1H), 6.70-6078 (m, 2H), 6.20-6.23 (bs, 1H), 5.97 (s, 2H), 3.59 (t, 4H, J=6.9 Hz), 1.95 (s, 4H).

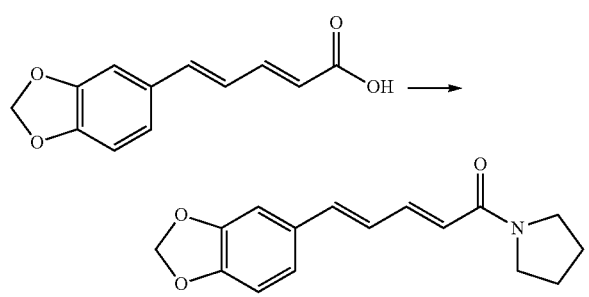

(2E,4E)-5-(benzo[d][1,3]dioxol-5-yl)-1-(pyrrolidin-1-yl)penta-2,4-diene-1-one (LJ-2487)

Synthesis of (E)-3-benz[d][1,3]dioxol-5-yl)pro-2-en-1-ol

Piperonal (2 g, 13.3 mmol) and (1-ethoxycarbonylmethylidine)triphenylphosphorane (9.28 g, 26.6 mmol) were mixed, and stirred in a solvent of $CH_2Cl_2$ at room temperature for 12 hours. Upon completion of the reaction, the solvent was removed through distillation under reduced pressure. The residue was dissolved in EtOAC and washed with $H_2O$ and a saturated solution of NaCl, followed by drying over anhydrous $Na_2SO_4$, and then the solvent was distilled under reduced pressure. The material containing impurities was purified by column chromatography (Hexane:EtOAc (2:1)) on silica gel to give a Wittig product (2.34, yield: 80%). The thus obtained Wittig product (950 mg, 4.31 mmol) was dissolved in toluene and cooled to −40° C., followed by slow addition of diisobutylaluminum hydride (DIBAL, 9.05 mL, 9.05 mmol). The reaction was carried out for 30 minutes under strictly anhydrous reaction conditions. After the reaction was terminated, the temperature was raised to room temperature while methanol (9 mL) was slowly added in an amount equal to that of DIBAL. The reaction mixture was diluted with EtOAc (30 mL), and filtered through celite under reduced pressure. The filtrate was distilled under reduced pressure, and then the residue was purified by column chromatography (hexane:EtOAc (4:1)) to give a target compound (702 mg, yield: 91.4%).

1H NMR (500 MHz, $CDCl_3$) d 6.92 (d, 1H, J=1.9 Hz), 6.81 (dd, 1H, J=1.8 Hz), 6.75 (d, 1H, J=7.8 Hz), 6.50-6.53 (m, 1H), 6.16-6.22 (ddd, 1H, J=4.2 Hz), 5.95 (s, 2H), 4.29 (dd, 2H, J=1.4 Hz).

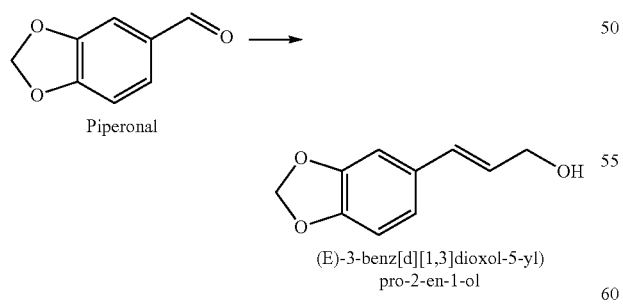

Piperonal (E)-3-benz[d][1,3]dioxol-5-yl)pro-2-en-1-ol

Synthesis of (E)-3-benz[d][1,3]dioxol-5-yl)allyl acetate (LJ-2196)

(E)-3-benz[d][1,3]dioxol-5-yl)pro-2-en-1-ol (200 mg, 1.12 mmol) was dissolved in $CH_2Cl_2$, and then anhydrous acetic acid (0.127 mL, 1.34 mmol) and DMAP (137.4 mg, 1.12 mmol) were sequentially added thereto, followed by stirring at room temperature for 30 minutes. Upon completion of the reaction, the solvent was distilled under reduced pressure, followed by washing with distilled water and a saturated solution of NaCl, drying over anhydrous $Na_2SO_4$, and then filtering. The filtrate was distilled under reduced pressure. The obtained residue was purified by column chromatography (hexane:EtOAc (4:1)) to give a target compound (246 mg, yield: 99.7%).

1H NMR (500 MHz, $CDCl_3$) d 6.92 (d, 1H, J=1.9 Hz), 6.81 (dd, 1H, J=1.4 Hz), 6.75 (d, 1H, J=7.8 Hz), 6.53-6.57 (bs, 1H), 6.08-6.13 (ddd, 1H, J=2.3 Hz), 5.95 (s, 2H), 4.68 (dd, 2H, J=1.4 Hz), 2.08 (s, 3H).

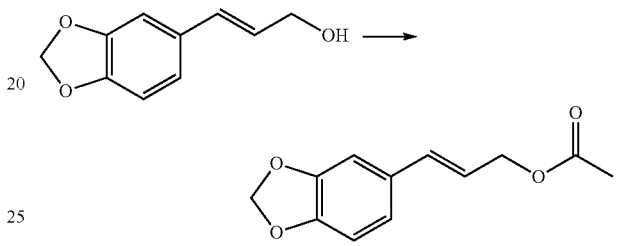

(E)-3-benz[d][1,3]dioxol-5-yl)allyl acetate (LJ-2196)

Synthesis of (E)-ethyl 4-(diethoxyphosphoryl)but-2-enoate

Triethyl phosphite (3.21 mL, 18.6 mmol) was added to methyl 4-bromocrotonic acid (3.0 g, 15.5 mmol) and the mixture was stirred at 100° C. for 4 hours. Upon completion of the reaction, the mixed solution was purified by column chromatography (hexane:EtOAc=6:1→EtOAc:acetone=1:1) to give a target compound (2.36 g, yield: 86.4%).

1H NMR (500 MHz, $CDCl_3$) d 6.82-6.90 (ddd, 1H, J=8.3 Hz), 5.92-5.97 (m, 1H), 4.18 (t, 2H, J=6.0 Hz), 4.06-4.15 (m, 4H), 2.70-2.76 (m, 2H), 1.24 (m, 9H).

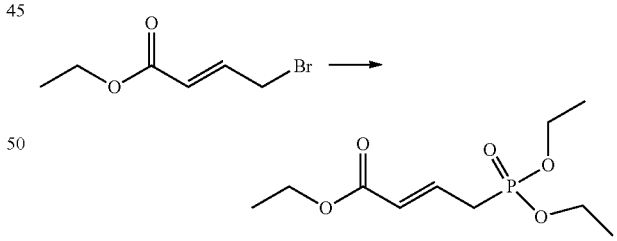

(E)-ethyl 4-(diethoxyphosphoryl)but-2-enoate

Synthesis of (E)-4-(diethoxyphosphoryl)but-2-enoate (E)-methyl 4-(diethoxyphosphoryl)but-2-enoate (3.35 g, 13.4 mmol) was dissolved in THF (25 mL), and LiOH (353.5 mg, 14.76 mmol) was added thereto, followed by stirring at room temperature for 30 minutes. After the reaction was completed, the pH was adjusted to about 4, followed by extraction with EtOAc, washing with a saturated solution of NaCl, drying over anhydrous $Na_2SO_4$, and then filtering. The filtrate was distilled under reduced pressure to give a target compound (2.46 g, yield: 82.63%).

1H NMR (500 MHz, CDCl$_3$) d 6.90-6.98 (ddd, 1H, J=7.8 Hz), 5.94-5.98 (m, 1H), 4.09-4.15 (m, 4H), 2.74-2.80 (m, 2H), 1.32 (t, 6H, J=6.9 Hz).

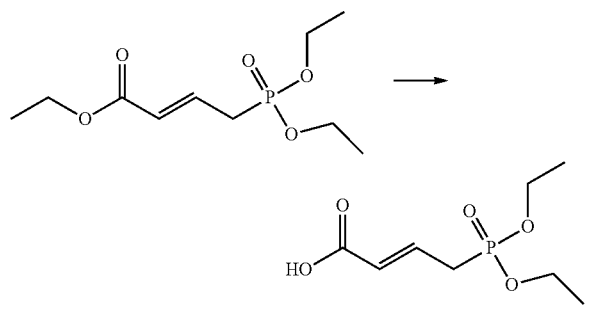

(E)-4-(diethoxyphosphoryl)but-2-enoate

Synthesis of (E)-diethyl 4-oxo-4-(piperidin-1-yl)but-2-enylphosphoric acid (E)-4-(diethoxyphosphoryl)but-2-enoate (2.42 g, 10.92 mmol) was dissolved in CH$_2$Cl$_2$, and then piperidine (1.61 mL, 16.38 mmol), triethylamine (2.28 mL, 16.38 mmol), and DMAP (133.5 mg, 1.09 mmol) were sequentially added thereto. After about 10 minutes, EDAC (2.29 g, 12.01 mmol) was added to the mixed solution, followed by stirring at room temperature for 4 hours. Upon completion of the reaction, the solvent was removed through distillation under reduced pressure, followed by washing with 1N HCl and a solution of NaHCO$_3$. The oil layer was separated, followed by washing with distilled water and a saturated solution of NaCl and drying over anhydrous Na$_2$SO$_4$, and then the thus obtained residue was purified by column chromatography (hexane:EtOAc (1:1)) to give a target compound (2.38 g, yield: 75.4%).

1H NMR (500 MHz, CDCl$_3$) d 6.70-6.78 (ddd, 1H, J=7.8 Hz), 6.41-6.45 (m, 1H), 4.07-4.13 (m, 4H), 3.55 (t, 4H, J=5.5 Hz), 2.72-2.78 (m, 2H), 1.62 (m, 2H), 1.55-1.59 (m, 4H), 1.29-1.33 (m, 6H).

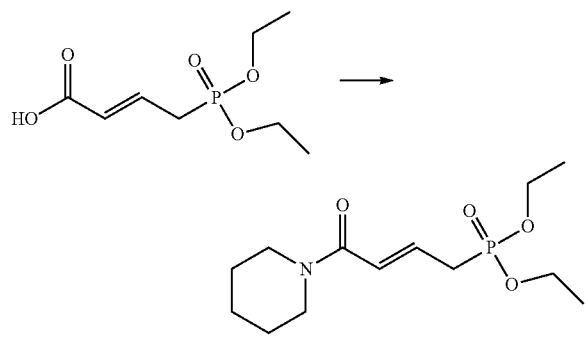

(E)-diethyl 4-oxo-4-(piperidin-1-yl)but-2-enylphosphoric acid

Synthesis of (2E,4E)-5-(2,5-dimethoxyphenyl)-1-(piperidin-1-yl)penta-2,4-diene-1-one (LJ-2488)

(E)-diethyl 4-oxo-4-(piperidin-1-yl)but-2-enylphosphoric acid (50 mg, 0.17 mmol) and 2,5-dimethoxybenzaldehyde (28.4 mg, 0.17 mmol) were dissolved in THF (1.5 mL) at −10° C., and then potassium tert-butoxide (0.51 mL, 0.51 mmol) was added thereto, followed by stirring at the same temperature for 20 minutes under anhydrous reaction conditions. The temperature of the mixture was raised to room temperature, and the reaction was terminated by the addition of distilled water. After EtOAc was added, the oil layer was separated, followed by washing with distilled water and a saturated solution of NaCl, drying over anhydrous Na$_2$SO$_4$, and then filtering. The filtrate was distilled under reduced pressure, and the thus obtained residue was purified by column chromatography (hexane:EtOAc (2:1)) to give a target compound (40.7 mg, yield: 78.6%).

1H NMR (500 MHz, CDCl$_3$) d 7.48-6.53 (dd, 1H, J=3.2 Hz), 7.16-7.19 (bs, 1H), 7.02 (bs, 1H), 6.88-6.95 (m, 1H), 6.81 (d, 1H, J=3.2 Hz), 6.42-6.48 (bs, 2H), 3.81 (s, 4H), 3.78 (s, 3H), 3.59 (t, 4H, J=3.2 Hz), 1.66 (m, 2H), 1.56-1.60 (m, 4H).

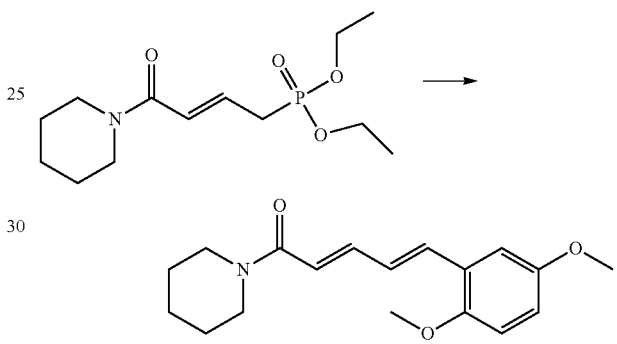

(2E,4E)-5-(2,5-dimethoxyphenyl)-1-(piperidin-1-yl)penta-2,4-diene-1-one (LJ-2488)

Synthesis of (2E,4E)-5-(2,3-dimethoxyphenyl)-1-(piperidin-1-yl)penta-2,4-diene-1-one (LJ-2489)

(E)-diethyl 4-oxo-4-(pipelidin-1-yl)but-2-enylphosphoric acid (50 mg, 0.17 mmol) and 2,3-dimethoxybenzaldehyde (28.4 mg, 0.17 mmol) were used as starting materials, and the synthesis was conducted by the same method as LJ-2488, thereby giving a target compound (41.2 mg, yield: 79.5%).

1H NMR (500 MHz, CDCl$_3$) d 7.47-6.52 (dd, 1H, J=3.7 Hz), 7.17-7.25 (bs, 1H), 7.11 (dd, 1H, J=0.9 Hz), 7.02 (m, 2H), 6.85 (t, 1H, J=1.5 Hz), 6.41-6.47 (m, 1H), 3.85 (s, 3H), 3.81 (s, 3H), 3.59 (t, 4H, J=5.5 Hz), 1.65 (m, 2H), 1.59 (m, 4H).

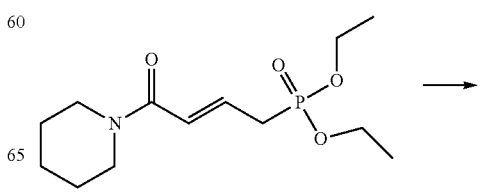

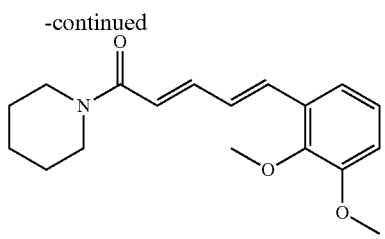

(2E,4E)-5-(2,3-dimethoxyphenyl)-1-(piperidin-1-yl)
penta-2,4-diene-1-one (LJ-2489)

Synthesis of (2E,4E)-5-(2,4-dimethoxyphenyl)-1-(piperidin-1-yl)penta-2,4-diene-1-one (LJ-2490)

(E)-diethyl 4-oxo-4-(pipelidin-1-yl)but-2-enylphosphoric acid (50 mg, 0.17 mmol) and 2,4-dimethoxybenzaldehyde (28.4 mg, 0.17 mmol) were used as starting materials, and the synthesis was conducted by the same method as LJ-2488, thereby giving a target compound (39.8 mg, yield: 76.8%).

1H NMR (500 MHz, CDCl$_3$) d 7.49-6.54 (dd, 1H, J=3.7 Hz), 7.39 (d, 1H, J=8.3 Hz), 7.10-7.14 (d, 1H, J=15.6 Hz), 6.81-6.89 (m, 1H), 6.48 (dd, 1H, J=6.0 Hz), 6.43 (d, 1H, J=2.3 Hz), 6.36 (d, 1H, J=14.7 Hz), 3.84 (s, 3H), 3.82 (s, 3H), 3.60 (t, 4H, J=14.7 Hz), 1.65 (m, 2H), 1.59 (m, 4H).

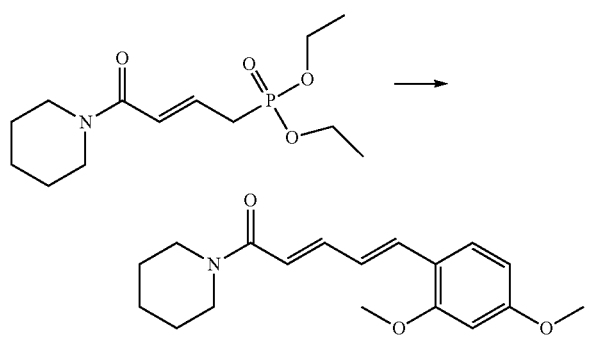

(2E,4E)-5-(2,4-dimethoxyphenyl)-1-(piperidin-1-yl)penta-2,4-diene-1-one (LJ-2490)

Synthesis of (2E,4E)-5-(3,4-dimethoxyphenyl)-1-(piperidin-1-yl)penta-2,4-diene-1-one (LJ-2491)

(E)-diethyl 4-oxo-4-(pipelidin-1-yl)but-2-enylphosphoric acid (50 mg, 0.17 mmol) and 3,4-dimethoxybenzaldehyde (28.4 mg, 0.17 mmol) were used as starting materials, and the synthesis was conducted by the same method as LJ-2488, thereby giving a target compound (39.6 mg, yield: 76.5%).

1H NMR (500 MHz, CDCl$_3$) d 7.40-6.45 (m, 1H), 7.23 (bs, 1H), 6.97-7.01 (ddd, 1H, J=2.3 Hz), 6.83 (d, 1H, J=8.3 Hz), 6.78 (t, 2H, J=4.2 Hz), 6.43-6.46 (d, 1H, J=14.7 Hz), 3.90 (s, 3H), 3.80 (s, 3H), 3.58 (bs, 4H), 1.65 (m, 2H), 1.58 (m, 4H).

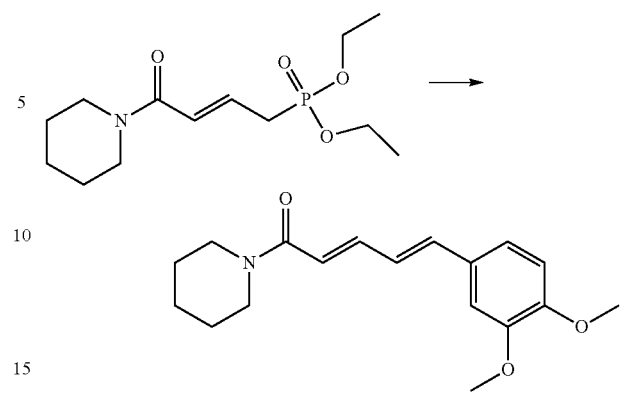

2E,4E)-5-(3,4-dimethoxyphenyl)-1-(piperidin-1-yl)
penta-2,4-diene-1-one (LJ-2491)

Synthesis of (2E,4E)-5-(3,5-dimethoxyphenyl)-1-(piperidin-1-yl)penta-2,4-diene-1-one (LJ-2492)

(E)-diethyl 4-oxo-4-(pipelidin-1-yl)but-2-enylphosphoric acid (50 mg, 0.17 mmol) and 3,5-dimethoxybenzaldehyde (28.4 mg, 0.17 mmol) were used as starting materials, and the synthesis was conducted by the same method as LJ-2488, thereby giving a target compound (41.8 mg, yield: 80.5%).

1H NMR (500 MHz, CDCl$_3$) d 7.40-6.45 (dd, 1H, J=3.7 Hz), 6.84-6.89 (dd, 1H, J=4.6 Hz), 6.75-6.79 (d, 1H, J=15.6 Hz), 6.59 (d, 2H, J=2.3 Hz), 6.47 (d, 1H, J=14.7 Hz), 6.40 (t, 1H, J=2.3 Hz), 3.80 (s, 6H), 3.58 (bs, 4H), 1.66 (m, 2H), 1.59 (m, 4H).

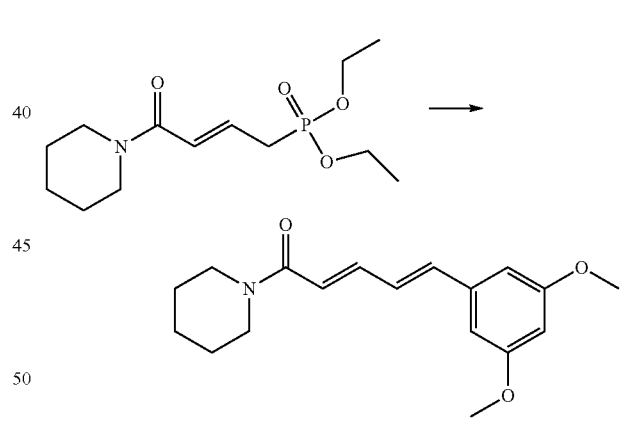

(2E,4E)-5-(3,5-dimethoxyphenyl)-1-(piperidin-1-yl)
penta-2,4-diene-1-one (LJ-2492)

Synthesis of trans-(LJ-2497) and cis-(2E,4E)-5-(2,5-dimethylphenyl)-1-(piperidin-1-yl)penta-2,4-diene-1-one (LJ-2498)

(E)-diethyl 4-oxo-4-(pipelidin-1-yl)but-2-enylphosphoric acid (50 mg, 0.17 mmol) and 2,5-dimethoxybenzaldehyde (23.1 mg, 0.17 mmol) were used as starting materials, and the synthesis was conducted by the same method as LJ-2488, thereby giving a trans-isomer (24.9 mg, yield: 50.6%) and a cis-isomer (12.6 mg, yield: 27.3%).

Trans-(2E,4E)-5-(2,5-dimethoxyphenyl)-1-(piperidin-1-yl)penta-2,4-diene-1-one (LJ-2497)

1H NMR (500 MHz, CDCl₃) d 7.40-6.45 (dd, 1H, J=3.7 Hz), 7.27 (bs, 1H), 7.19 (dd, 1H, J=3.7 Hz), 6.93-7.04 (ddd, 2H, J=6.5 Hz), 6.71-6.77 (m, 1H), 6.39 (m, 1H), 3.53 (bs, 4H), 2.25 (s, 6H), 1.60 (m, 2H), 1.53 (m, 4H).

Cis-(2E,4E)-5-(2,5-dimethoxyphenyl)-1-(piperidin-1-yl)penta-2,4-diene-1-one (LJ-2498)

1H NMR (500 MHz, CDCl₃) d 7.42-6.48 (ddd, 1H, J=3.2 Hz), 7.20 (d, 1H, J=5.1 Hz), 6.99 (d, 1H, J=8.3 Hz), 6.93 (t, 1H, J=7.8 Hz), 6.69-6.72 (dd, 1H, J=11.5 Hz), 6.39 (dd, 1H, J=15.1 Hz), 6.32 (ddd, 1H, J=11.0 Hz), 3.49 (t, 4H, J=5.5 Hz), 2.26 (s, 3H), 2.14 (s, 3H), 1.58 (m, 2H), 1.52 (m, 4H).

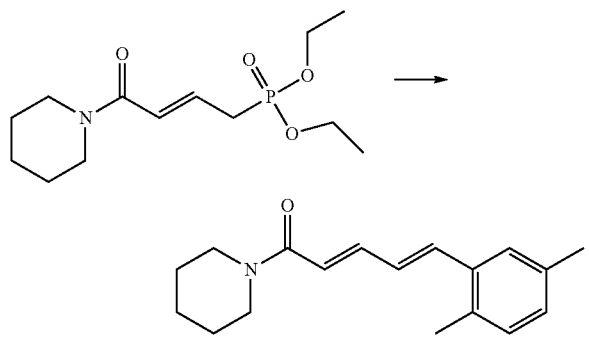

Trans-(2E,4E)-5-(2,5-dimethoxyphenyl)-1-(piperidin-1-yl)penta-2,4-diene-1-one (LJ-2497) and cis-(2E,4E)-5-(2,5-dimethoxyphenyl)-1-(piperidin-1-yl)penta-2,4-diene-1-one (LJ-2498)

Synthesis of (E)-N-(benz[d][1,3]dioxol-5-ylmethylene)aniline (LJ-2477)

Piperonal (0.63 g, 4.22 mmol), ethanol (4 ml), and aniline (0.38 g, 4.22 mmol) were put in a 25 ml flask, and acetic acid (10 ml) was slowly added dropwise thereto while the mixture was stirred under nitrogen charging conditions, followed by stirring at 80° C. for 12 hours. Then, the temperature of the mixture was lowered to 0° C., followed by the addition of a little water to obtain a solid. The filtering was performed while the solid was washed with cool ethanol, thereby giving clean E)-N-(benz[d][1,3]dioxol-5-ylmethylene)aniline (LJ-2477) with a yield of 45%.

1H NMR (300 MHz, CDCl₃) d 6.04 (s, 2H), 6.88 (d, 1H, J=8.1 Hz), 7.17-7.30 (m, 4H), 7.29-7.41 (m, 2H), 7.53 (d, 1H, J=1.5 Hz), 8.33 (s, 1H).

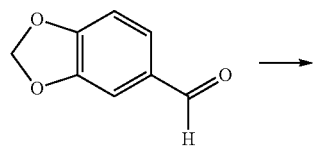

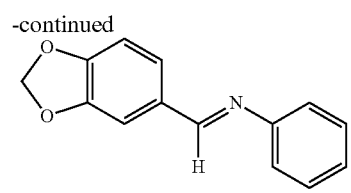

(E)-N-(benz[d][1,3]dioxol-5-ylmethylene)aniline (LJ-2477)

Synthesis of (E)-5-(((6bromobenzo[d][1,3]dioxol-5-yl)methyleneamino)-1H-benzo[d]imidazole-2(3H)-one (LJ-2527)

6-bromobenzo[d][1,3]dioxol-5-carbaldehyde (0.63 g, 1.31 mmol), IPA (6 ml), and 5-amino-1H-benzo[d]imidazole-2(3H)-one (0.2 g, 1.31 mmol) were put in a 25 ml flask, and acetic acid (10 ml) was slowly added dropwise thereto while the mixture was stirred under nitrogen charging conditions, followed by stirring for 12 hours under reflux conditions. After that, the temperature of the mixture was lowered to room temperature, and the thus obtained solid was washed with methylene chloride and methanol, followed by filtering, thereby obtaining clean (E)-5-((6bromobenzo[d][1,3]dioxol-5-yl)methyleneamino)-1H-benzo[d]imidazole-2(3H)-one at 95% yield.

1H NMR (300 MHz, DMSO) d 6.19 (s, 2H), 6.91-7.01 (m, 3H), 7.36 (s, 1H), 7.60 (s, 1H), 8.71 (s, 1H), 10.67 (bs, 2H).

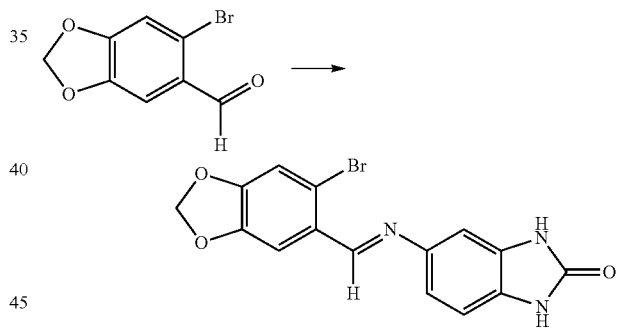

(E)-5-((6bromobenzo[d][1,3]dioxol-5-yl)methyleneamino)-1H-benzo[d]imidazole-2(3H)-one (LJ-2527)

Synthesis of (E)-5-((5-bromobenzo[d][1,3]dioxol-4-yl)methyleneamino)-1H-benzo[d]imidazole-2(3H)-one (LJ-2529)

5-bromobenzo[d][1,3]dioxol-4-carbaldehyde (0.25 g, 1.09 mmol), IPA (5 ml), and 5-amino-1H-benzo[d]imidazole-2(3H)-one (0.16 g, 1.09 mmol) were put in a 25 ml flask, and acetic acid (10 ml) was slowly added dropwise thereto while the mixture was stirred under nitrogen charging conditions, followed by stirring for 12 hours under reflux conditions. After that, the temperature of the mixture was lowered to room temperature, and the thus obtained solid was washed with methylene chloride and methanol, followed by filtering, thereby obtaining clean (E)-5-((6bromobenzo[d][1,3]dioxol-4-yl)methyleneamino)-1H-benzo[d]imidazole-2(3H)-one at 80% yield.

1H NMR (300 MHz, DMSO) d 6.20 (s, 1H), 6.86-6.99 (m, 4H), 7.20 (d, 1H, J=8.4 Mz), 8.69 (s, 1H), 10.68 (s, 1H).

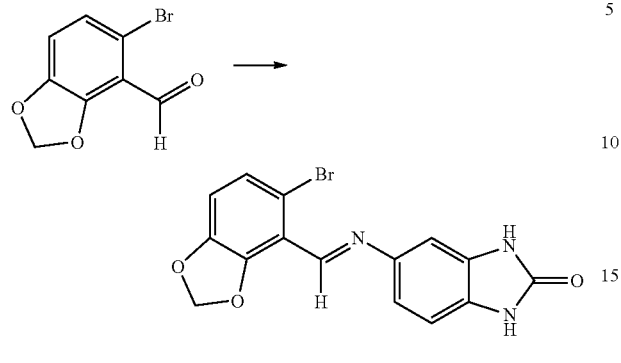

(E)-5-((5-bromobenzo[d][1,3]dioxol-4-yl)methyleneamino)-1H-benzo[d]imidazole-2(3H)-one (LJ-2529)

Synthesis of (E)-5-((5-bromobenzo[d][1,3]dioxol-4-yl)methyleneamino)-1H-benzo[d]imidazole-2(3H)-thione (SKKU-S-02)

5-bromobenzo[d][1,3]dioxol-4-carbaldehyde (0.24 g, 1.05 mmol), IPA (4.8 ml), and 5-amino-1H-benzo[d]imidazole-2(3H)-thione (0.2 g, 1.21 mmol) were put in a 25 ml flask, and acetic acid (10 ml) was slowly added dropwise thereto while the mixture was stirred under nitrogen charging conditions, followed by stirring for 12 hours under reflux conditions. After that, the temperature of the mixture was lowered to room temperature, and the thus obtained solid was washed with methylene chloride and methanol, followed by filtering, thereby obtaining clean (E)-5-(((6bromobenzo[d][1,3]dioxol-4-yl)methyleneamino)-1H-benzo[d]imidazole-2(3H)-thione at 83% yield.

1H NMR (300 MHz, DMSO) d 6.21 (s, 2H), 6.99-7.09 (m, 3H), 7.20 (t, 2H), 8.66 (s, 1H), 12.58 (bs, 2H).

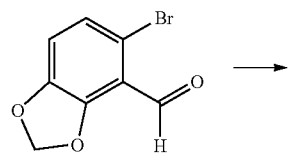

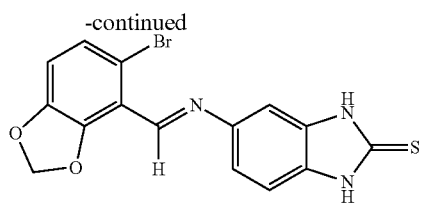

(E)-5-((5-bromobenzo[d][1,3]dioxol-4-yl)methyleneamino)-1H-benzo[d]imidazole-2(3H)-thione (SKKU-S-02)

Example 2

Inhibitory Efficacy of Piperine-Based Compound on Adipocyte Differentiation in Mouse Adipocyte Line (3T3-L1)

1) Cell Culture and Oil-Red O Staining

Mouse adipocyte line (3T3-L1) was used to evaluate effects of various piperine-based compounds on adipocyte differentiation and growth. 3T3-L1 cells as preadipocytes were dispensed on a 12-well plate, and cultured in a 5% $CO_2$ incubator using DMEM medium supplemented with 1% penicillin-streptomycin, 1% non-essential amino acids, and 10% FBS. The cultured 3T3-L1 cells were made into differentiated adipocytes by being cultured for 2 hours in a medium containing 0.5 mM isobutyl-methyl xanthic acid, 1 μM dexamethasone (MDI), and 1 μg/mL insulin, and then differentiated into mature adipocytes by being further cultured in a medium 1 μg/mL insulin. After that, they were further cultured for 10 days while changing the DMEM culture liquid every other day to obtain fully differentiated adipocytes.

The culture liquid was treated with 13 new compounds with different concentrations every other day from day 0 when DMI was added to the 3T3-L1 cells for differentiation. Structures and molecular weights of the total of 13 new compounds were shown in Table 1. Derivative compounds were dissolved in DMSO before the use thereof, and a negative control group added with only DMSO was included in the experiment.

After the culturing for a total of 14 days, the culture liquids were removed when the cells were fully differentiated, and fat spheres contained in the differentiated adipocytes were stained. For this, the cells were washed 2 times with phosphate buffered saline (PBS), immobilized in 10% buffered neutral formalin for 1 hour, washed again once with PBS, stained for 1 hour by adding 1 mL of Oil-Red-O, which specifically stains fats red, to the 12-well plate, and then washed 2 times with distilled water. In order to measure the level of triglyceride contained in the differentiated 3T3-L1 cells, the stained cells were dissolved in 1 mL of iso-butanol and the OD value was measured at 600 nm.

TABLE 1

Structure of novel piperine derivatives

| No. | Derivatives | Chemical Name | Structure | Molecular weight(g/mol) |
|---|---|---|---|---|
| 1 | LJ-2196 | (E)-3-(benzo[d][1,3]dioxo-5-yl)allyl acetate | 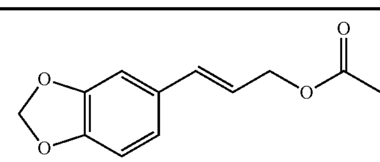 | 220.22 |

TABLE 1-continued

Structure of novel piperine derivatives

| No. | Derivatives | Chemical Name | Structure | Molecular weight(g/mol) |
|---|---|---|---|---|
| 2 | LJ-2477 | (E)-N-(benzo[d][1,3]dioxol-5-ylmethylene)aniline | 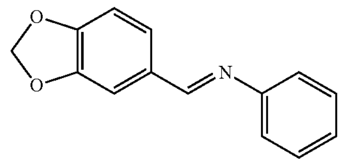 | 225.24 |
| 3 | LJ-2487 | (2E,4E)-5-(benzo[d][1,3]dioxol-5-yl)-1-(pyrrolidin-1-yl)penta-2,4-dien-1-one | 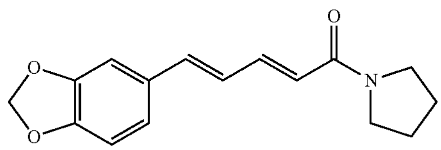 | 271.31 |
| 4 | LJ-2488 | (2E,4E)-5-(2,5-dimethoxyphenyl)-1-(piperidin-1-yl)penta-2,4-dien-1-one | 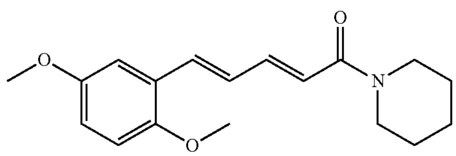 | 301.38 |
| 5 | LJ-2489 | (2E,4E)-5-(2,3-dimethoxyphenyl)-1-(piperidin-1-yl)penta-2,4-dien-1-one | 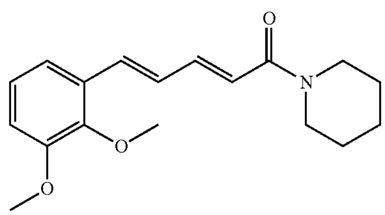 [SMILES: COc1cccc(/C=C/C=C/C(=O)N2CCCCC2)c1OC] | 301.38 |
| 6 | LJ-2490 | (2E,4E)-5-(2,4-dimethoxyphenyl)-1-(piperidin-1-yl)penta-2,4-dien-1-one | 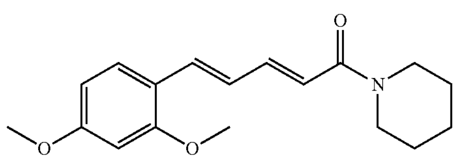 [SMILES: COc1ccc(/C=C/C=C/C(=O)N2CCCCC2)c(OC)c1] | 301.38 |
| 7 | LJ-2491 | (2E,4E)-5-(3,4-dimethoxyphenyl)-1-(piperidin-1-yl)penta-2,4-dien-1-one | 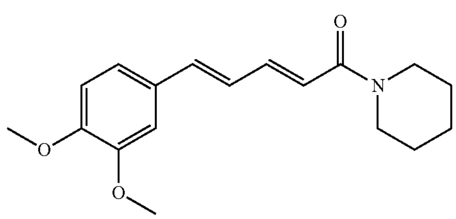 [SMILES: COc1ccc(/C=C/C=C/C(=O)N2CCCCC2)cc1OC] | 301.38 |
| 8 | LJ-2492 | (2E,4E)-5-(3,5-dimethoxyphenyl)-1-(piperidin-1-yl)penta-2,4-dien-1-one | 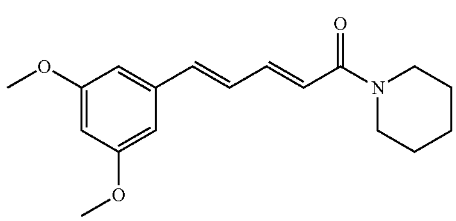 [SMILES: COc1cc(/C=C/C=C/C(=O)N2CCCCC2)cc(OC)c1] | 301.38 |
| 9 | LJ-2497 | Trans-(2E,4E)-5-(2,5-dimethylphenyl)-1-(piperidin-1-yl)penta-2,4-dien-1-one | 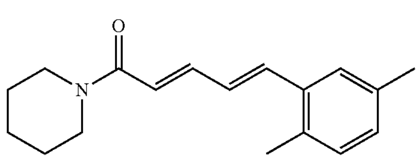 [SMILES: Cc1ccc(C)c(/C=C/C=C/C(=O)N2CCCCC2)c1] | 269.38 |

TABLE 1-continued

Structure of novel piperine derivatives

| No. | Derivatives | Chemical Name | Structure | Molecular weight(g/mol) |
|---|---|---|---|---|
| 10 | LJ-2498 | Cis-(2E,4E)-5-(2,5-dimethyl-phenyl)-1-(piperidin-1-yl) penta-2,4-dien-1-one | 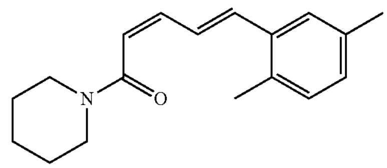 [SMILES: Cc1ccc(C)c(/C=C/C=C\C(=O)N2CCCCC2)c1] | 269.38 |
| 11 | LJ-2527 | (E)-5-(6-bromobenzo[d][1,3]dioxol-5-yl) methyleneamino)-1H-benzo[d]imidazol-2(3H)-one | 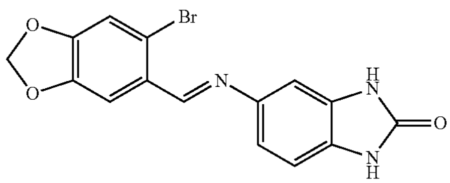 [SMILES: O=c1[nH]c2ccc(/N=C/c3cc4c(cc3Br)OCO4)cc2[nH]1] | 360.16 |
| 12 | LJ-2529 | (E)-5-(5-bromobenzo[d][1,3]dioxol-4-yl) methyleneamino)-1H-benzo[d]imidazol-2(3H)-one | 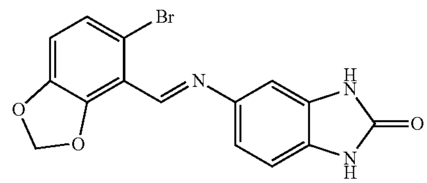 [SMILES: O=c1[nH]c2ccc(/N=C/c3c(Br)ccc4c3OCO4)cc2[nH]1] | 360.16 |
| 13 | SKKU-S-02 | (E)-5-(5-bromobenzo[d][1,3]dioxol-4-yl) methyleneamino)-1H-benzo[d]imidazole-2(3H)-thione | 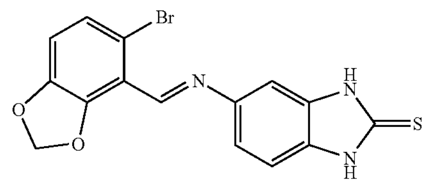 [SMILES: S=c1[nH]c2ccc(/N=C/c3c(Br)ccc4c3OCO4)cc2[nH]1] | 376.23 |

2) Inhibition of Adipocyte Differentiation by Novel Piperine Derivatives

Figure 1N:
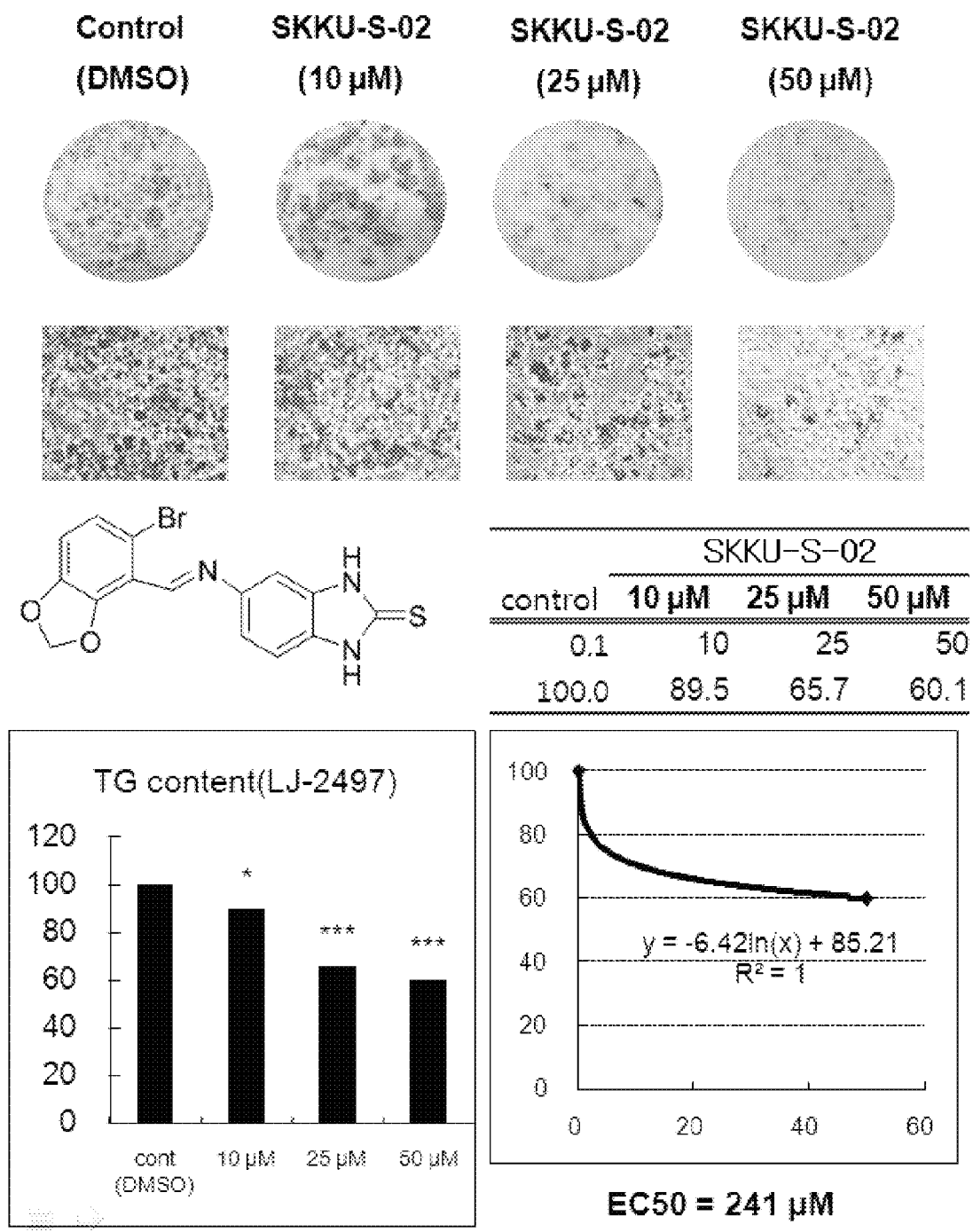

The 13 piperine derivatives (LJ-2196, LJ-2477, LJ-2487, LJ-2488, LJ-2489, LJ-2490, LJ-2491, LJ-2492, LJ-2497, LJ-2498, LJ-2527, LJ-2529 and SKKU-S-02) reduced the differentiation of the preadipocytes 3T3L1 in a concentration-dependent manner (FIGS. 1a-1n). When the amount of the fats stained with Oil Red O was quantitated by spectrophotometry, the OD value also decreased in a concentration-dependent manner. For reference, inhibition of preadipocyte differentiation and intracellular triglyceride accumulation for the derivatives were compared with those for piperine.

Example 3

LJ-2498 Compound's Effect of Reducing Body Weight and Visceral Fat in Mouse

1) Preparation of Test Diet and Breeding of Test Animals

The obesity-inducing diet used in this example was high-fat diet (HFD: 40% fat calorie, 17 g lard+3% corn oil/100 g diet). LJ-2498 chemical (JL-2498) or piperine (Pin)-containing diet had the same composition as HFD, except that LJ-2498 chemical was included at 0.05%. As control drugs, metformin (Metf) as a diabetic treatment in a level of 0.1% and sibutramine as an obesity treatment in a level of 0.1% were added to a high-fat diet. A normal diet group (Chow) was fed with commercial rodent feedstuff.

TABLE 2

Composition of test diets

| Ingredients (g/kg diet) | High fat diet (HFD) | LJ-2498-containing diet (LJ2498) | Piperine-containing diet (Pin) | Sibutramin-containing diet (Sibut) | Metformin-containing diet (Metf) |
|---|---|---|---|---|---|
| Casein | 200 | 200 | 200 | 200 | 200 |
| DL-Methionine | 3 | 3 | 3 | 3 | 3 |
| Corn starch | 111 | 110.5 | 110.5 | 110 | 110.9 |
| Sucrose | 370 | 370 | 370 | 370 | 370 |
| Cellulose | 50 | 50 | 50 | 50 | 50 |
| Corn oil | 30 | 30 | 30 | 30 | 30 |
| Lard | 170 | 170 | 170 | 170 | 170 |

TABLE 2-continued

Composition of test diets

| Ingredients (g/kg diet) | High fat diet (HFD) | LJ-2498-containing diet (LJ2498) | Piperine-containing diet (Pin) | Sibutramin-containing diet (Sibut) | Metformin-containing diet (Metf) |
|---|---|---|---|---|---|
| Vitamin complex | 12 | 12 | 12 | 12 | 12 |
| Mineral complex | 42 | 42 | 42 | 42 | 42 |
| Choline bitartrate | 2 | 2 | 2 | 2 | 2 |
| Cholesterol | 10 | 10 | 10 | 10 | 10 |
| Tert-Butyl-hydroquinone | 0.04 | 0.04 | 0.04 | 0.04 | 0.04 |
| Test material | — | 0.5 | 0.5 | 0.1 | 1 |
| Total (g) | 1,000 | 1000 | 1000 | 1000 | 1000 |
| Fat (% calorie) | 39.0 | 39.0 | 39.0 | 39.0 | 39.0 |
| Total calorie, kJ/kg diet | 19,315 | 19,315 | 19,315 | 19,315 | 19,315 |

5-week-old male C57BL/6J mice (Orient, Korea) were accustomed to the laboratory environment for 1 week while feeding solid feed. Then, they were randomly divided into normal diet group, high-fat diet control group and test group of 3 types and control drug group of 2 types. They were bred for a total of 10 weeks (n=8/group). The diet was given between 10 and 11 a.m. every day together with water. Diet intake was measured every day and body weight was measured every week. In order to avoid transient body weight increase after feed intake, body weight was measured 2 hours after removing the feed. After fasting the test animal for at least 12 hours and anesthetizing with diethyl ether, blood, liver and visceral fat (epididymal fat, perirenal fat, mesenteric fat and retroperitoneal fat) were taken and weighed after washing with 0.1 M PBS (pH 7.4). Blood taken from the abdominal aorta was centrifuged at 1000×g for 15 minutes to separate the serum.

2) Body Weight and Visceral Fat Weight

Figure 2:
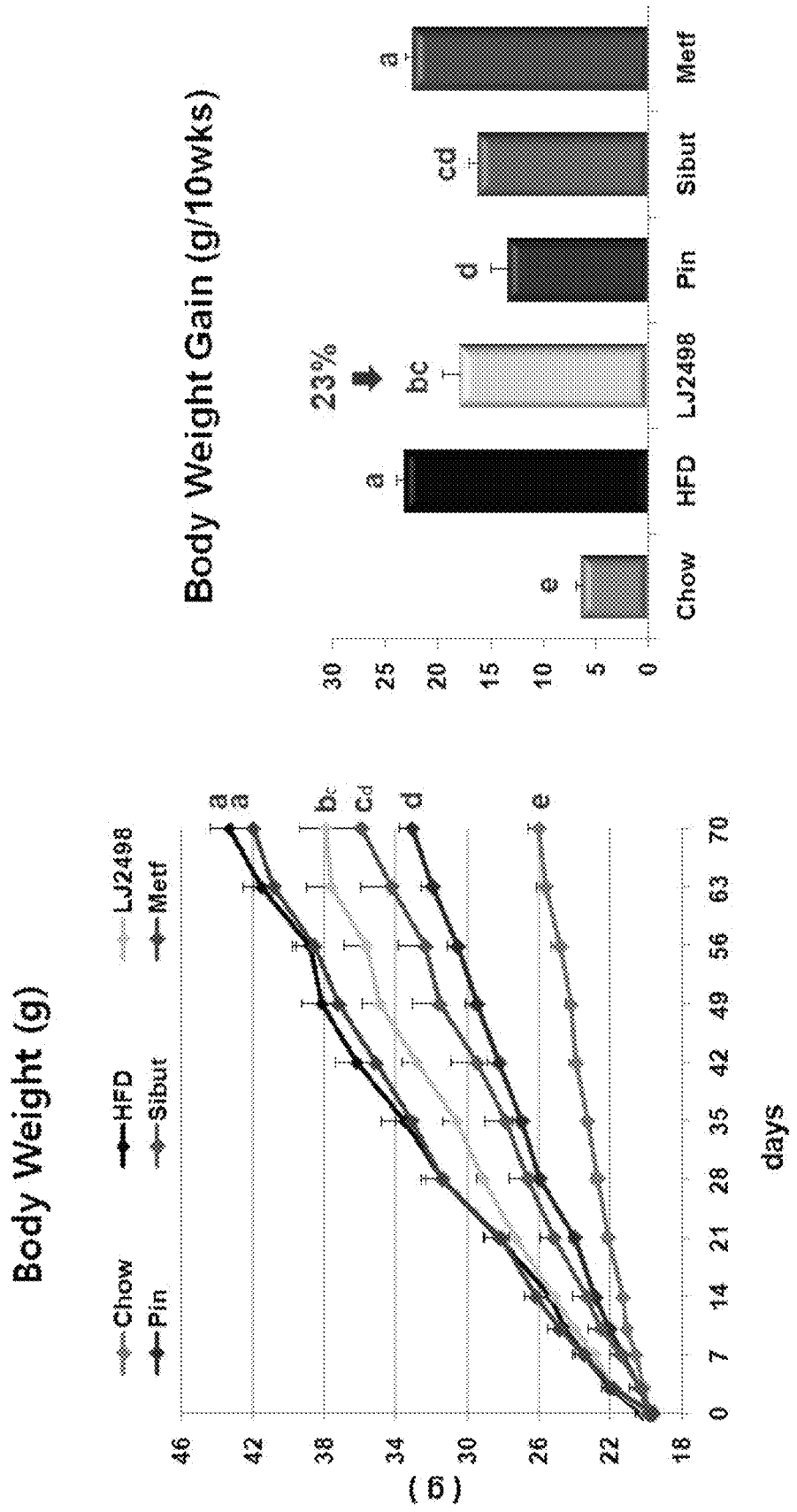
FIG. 2 shows body weight gain (g) of mice fed with test diets (LJ-2498).

After 10 weeks, the LJ-2498-administered group showed significantly lower accumulated body weight gain (23%) as compared to the high-fat diet control group (HFD) (see FIG. 2). Losing weight effect of piperine derivatives is similar or excellent compared to control drugs including metformin or sibutramin (see FIG. 2). FIG. 3 shows an abdomen open image of mice fed with test diets for 10 weeks. The LJ-2498-administered group showed significantly lower visceral fat weight as compared to the HFD group.

And, when the weight of epididymal fat, perirenal fat, mesenteric fat and retroperitoneal fat per body weight was measured, the LJ-2498-administered group showed significantly lower epididymal fat weight, perirenal fat weight, mesenteric fat weight, retroperitoneal fat weight and total visceral fat weight as compared to the control group (HFD). Total visceral fat weight (28%) of the LJ-2498-administered group was significantly lower compared to the control group (HFD) (see FIG. 3). Accordingly, it can be seen that LJ-2498 has excellent effect of reducing body weight and visceral fat.

Example 4

LJ-2498 Compound's Effect of Preventing and Treating Hyperlipidemia

1) Biochemical Analysis of Blood

After 10 weeks of breeding, total cholesterol, triglyceride and glucose levels in the plasma and lipid levels in the liver tissue were measured as follows. Total cholesterol, triglyceride, free fatty acid and glucose levels in the plasma were measured twice for each using a commercially available kit (Bio Clinical System). The activity of ALT (alanine aminotransferase) and AST (aspartate aminotransferase) used as liver function indicator were measured twice for each using a commercially available kit (Bio Clinical System, Korea).

2) Changes of Plasma Lipid Levels

Figure 4:
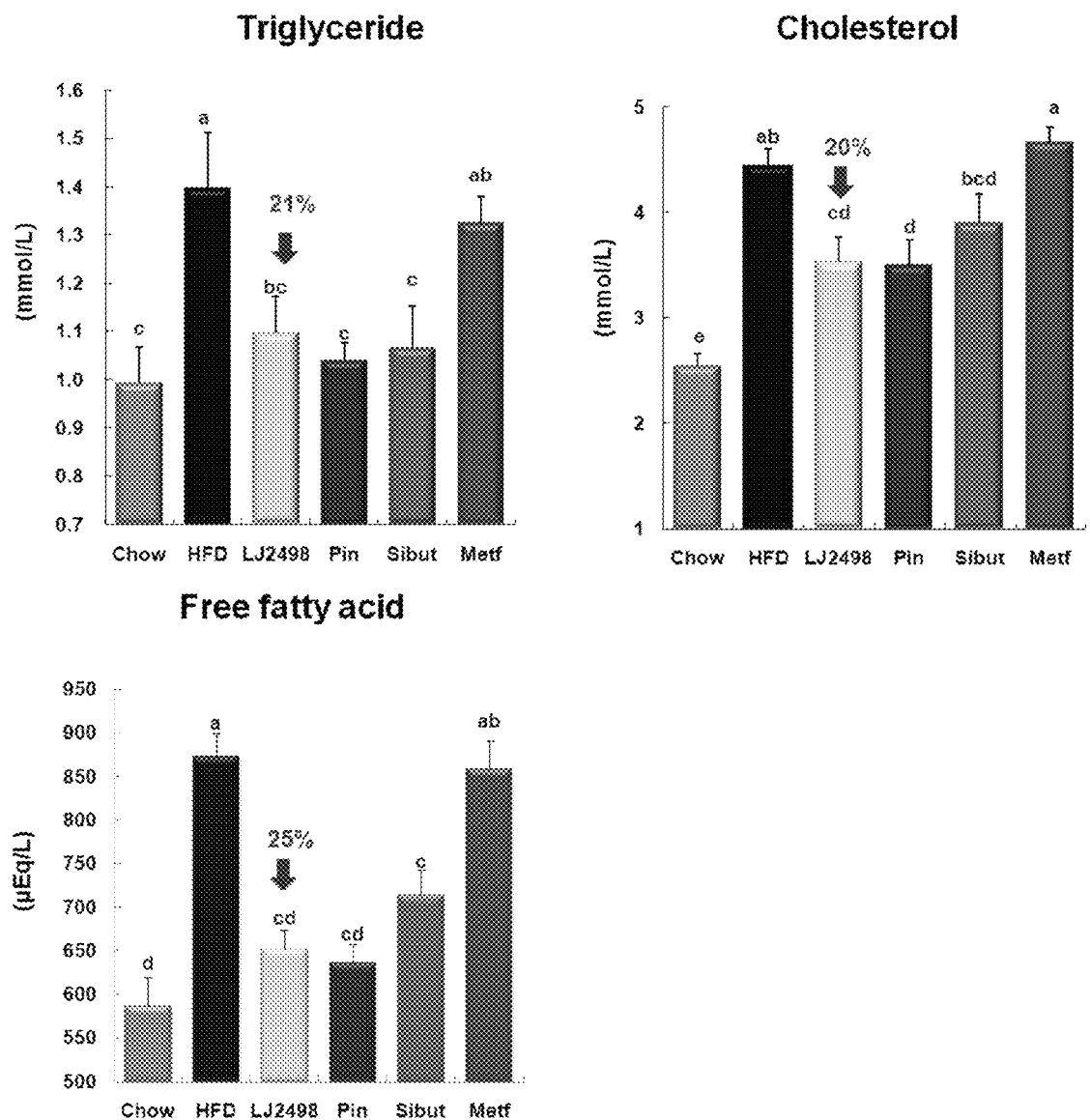
FIG. 4 shows blood lipid levels in mice fed with test diets (LJ-2498).
Figure 5:
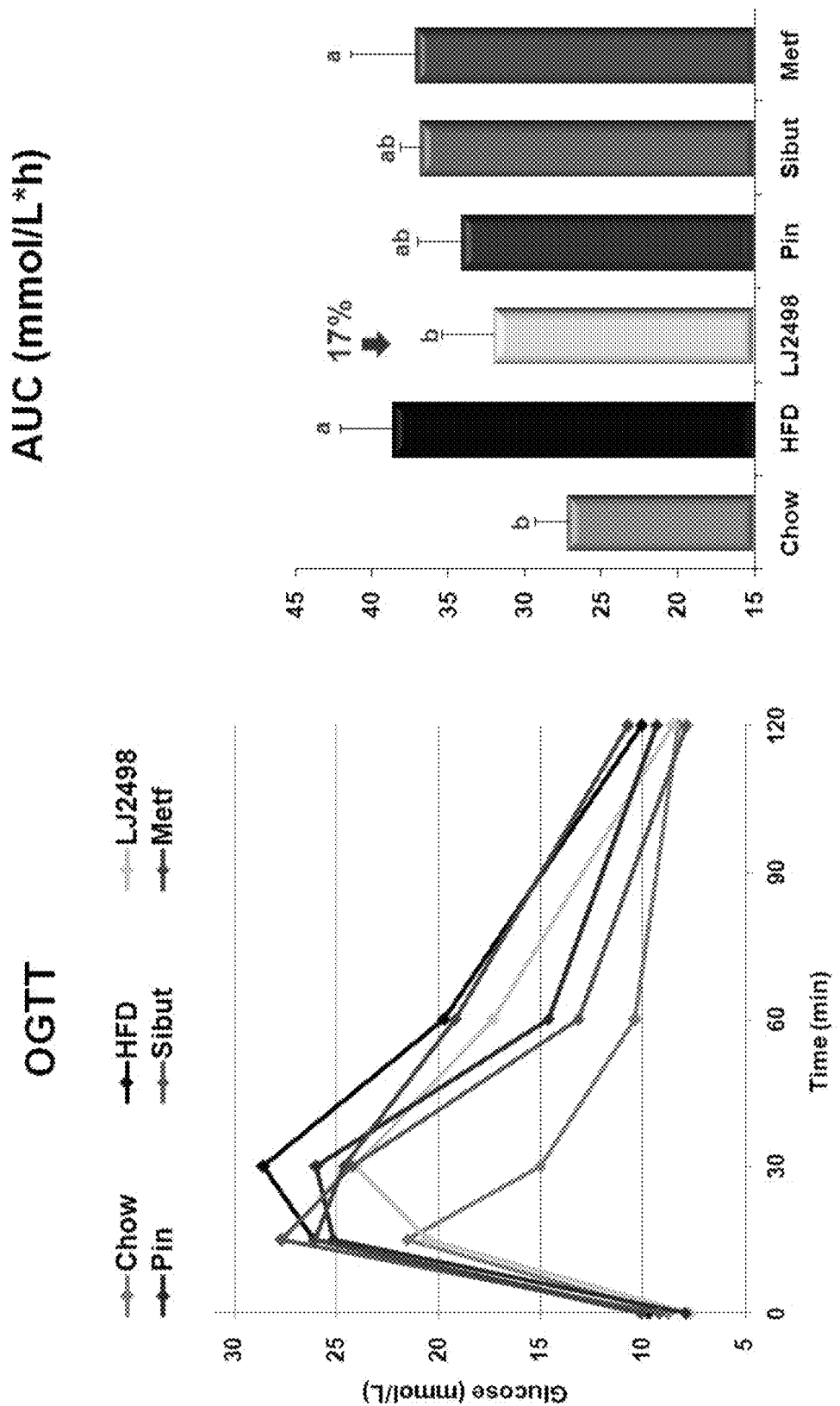
FIG. 5 represents results of oral glucose tolerance test for mice fed with test diets (LJ-2498).

After feeding the test diet for 10 weeks, the LJ-2498-administered group showed significantly lower plasma levels of triglyceride (by 21%), total cholesterol (by 20%), and free fatty acid (by 25%) as compared to the HFD group (FIG. 4). Accordingly, it could be recognized that LJ-2498 compound has the excellent effects of improving hyperlipidemia induced by the HFD.

Example 5

LJ-2498 Compound's Effect of Preventing and Treating Type 2 Diabetes

1) Oral Glucose Tolerance Test

After 8 weeks of experimental diet, the oral glucose tolerance test was performed on all groups. After 6 hours of fasting, the mice were orally administered with glucose (2 g glucose/10 ml of distilled water/kg body weight). Before the oral administration of glucose, at 15, 30, 60, and 120 min after the administration of glucose, blood samples were taken from the tail cut (by removing the distal 1 cm of the tail) and blood glucose concentrations were measured using a blood glucose monitoring device.

2) Oral Glucose Tolerance Test Results

As a result of the supplement intake of 8-week of the LJ-2498 compound to the mice fed with a high fat diet, the group significantly reduced the fasting blood glucose by 20% as compared with HFD group. Thus, it can be seen that the LJ-2498 compound inhibited the increase in the fasting blood glucose induced by a high-fat diet. The mice were orally administered with glucose (2 g glucose/10 ml of distilled water/kg body weight) and the blood glucose concentrations were measured from blood samples taken from the tail vein at intervals of 15, 30, 60, and 120 minutes. As a result, the blood glucose concentration was further reduced over all the time zones in the LJ-2498 compound treatment group as compared with the HFD group. In addition, the area under the curve (ACU) for blood glucose concentrations of the LJ-2489 compound treatment group was significantly reduced by 17% as compared with the HFD group. Therefore, it can be confirmed that the LJ-2489 compound had a remarkable effect in improving oral glucose tolerance. The insulin resistance improving effect of this LJ-2498 compound was shown to be more excellent than those of control drugs, metformin (Metf) and sibutramine.

Example 6

LJ-2498 Compound's Effect of Preventing and Treating Non-Alcoholic Fatty Liver

1) Analysis of Lipid Level in Liver Tissues

Lipids were extracted from the liver tissue according to Folch et al.'s method Folch J et al., J Biol. Chem. 226: 497-509 (1957)). After adding 1 mL of distilled water to 0.25 g of liver tissue, the liver tissue was homogenized using a Polytron homogenizer (IKA-Werke GmbH & Co., Ultra-Turrax, Staufen, Germany). After adding 5 mL of chloroform:methanol solution (2:1, v/v) to the homogenate and mixing well, the mixture was centrifuged at 1000×g for 10 minutes. After adding 2 mL of chloroform:methanol solution (2:1, v/v) again to the supernatant, the same procedure was repeated to completely separate the lipid components of the liver. After adding 3 mL of chloroform:methanl:0.05% $CaCl_2$ (3:48:47, v/v/v) solution to the remaining pellets and mixing well for 1 minute, followed by centrifugation at 1000×g for 10 minutes, the resulting pellets were completely dried with nitrogen gas. The dried lipids were dissolved in 1 mL of methanol and then analyzed.

The same kit (Bio Clinical System) as that used for the plasma analysis was used to measure the triglyceride and cholesterol levels of the liver tissue.

2) Changes of Liver Weight and Hepatic Lipid Levels

FIG. 6. represents the liver tissue images of mice fed with test diets for 10 weeks. HFD showed weak colored and bigger liver tissue as compared to Chow. Meanwhile, the LJ-2498-supplemented group showed darker and smaller liver tissue as compared to HFD that means improvement of fatty liver. The liver weight of LH-2498-supplemented group significantly decreased 23% compared to the HFD group (FIG. 6).

Figure 7:
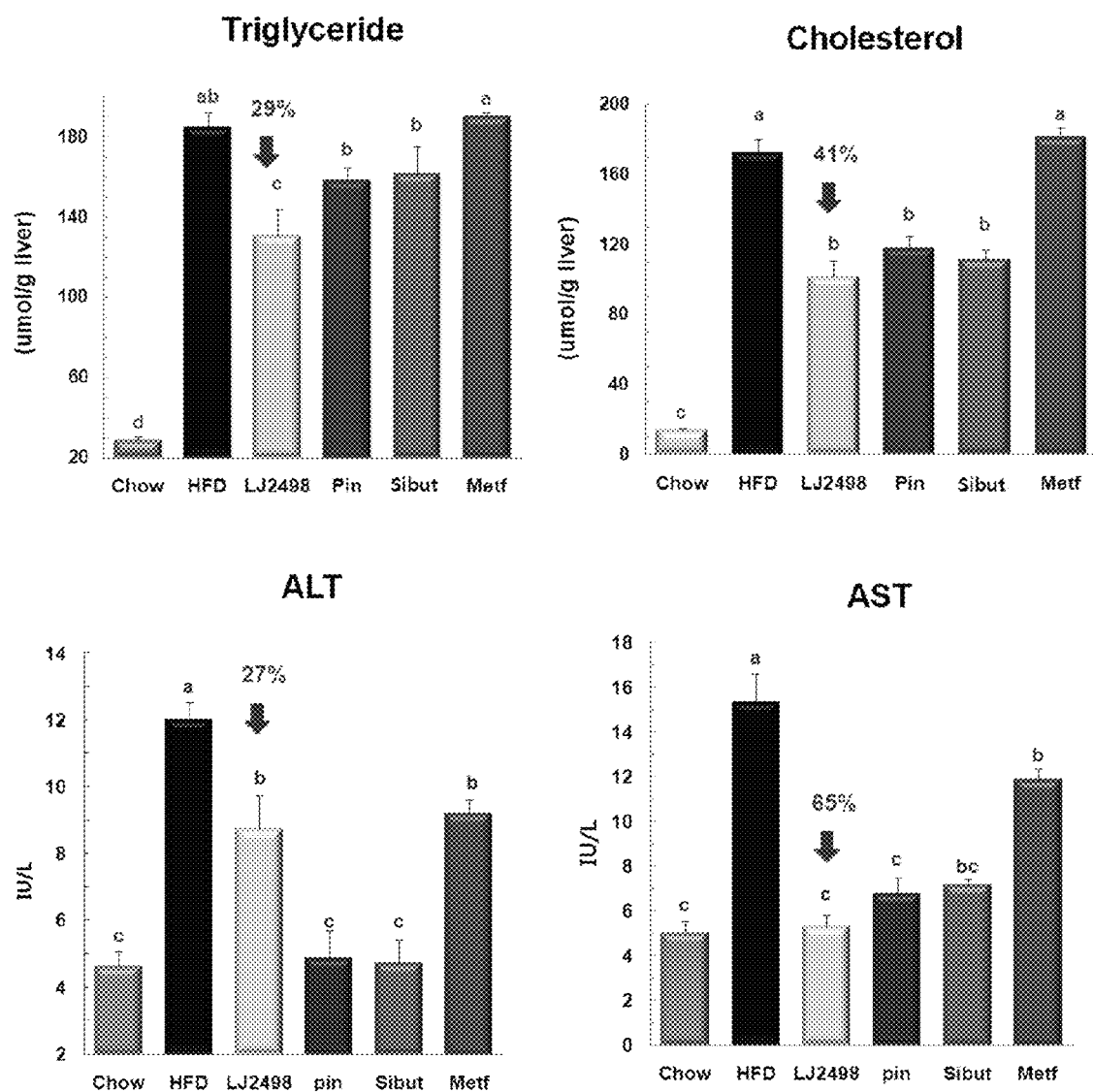
FIG. 7 shows a graph representing lipid levels of liver tissues of mice fed with test diets (LJ-2498).

The LJ-2498-supplemented group showed significantly decreased levels of triglyceride (by 29%) and cholesterol (by 41%) in liver tissue as compared to HFD (FIG. 7). Moreover, the HFD group exhibited significantly higher plasma activities of ALT (alanine aminotransferase) and AST (aspartate aminotransferase), which are parameters for hepatic function, as compared to the Chow group and the LJ-2498-supplemented group showed significantly decreased plasma activities of ALT (by 27%) and AST (by 15%) as compared to the HFD group (FIG. 7). Accordingly, it could be understood that LJ-2498 has the excellent effect of significantly improving fatty liver in obesity induced by HFD.

Example 7

Reduction of Body and Visceral Fat-Pad Weights by LJ-2529

1) Preparation of Test Diets and Maintenance of Test Animals

The obesity-inducing control diet used in the test was high-fat diet (HFD: 40% fat calorie, 17 g lard+3% corn oil/100 g diet). Diets supplemented with LJ-2529 compound or piperine had the same composition as HFD, except that LJ-2529 was included at 0.05%.

5-week-old male C57BL/6J mice (Orient, Korea) were accustomed to the laboratory environment for 1 week while feeding solid feed. Then, they were randomly divided into normal diet, high-fat diet and test groups of two types and bred for a total of 10 weeks (n=8/group). The diet was given between 10 and 11 a.m. every day together with water. Food intake was measured every day and body weight was measured once a week. In order to avoid transient body weight increase after feed intake, body weight was measured 2 hours after removing the feed. After fasting the test animal for at least 12 hours and anesthetizing with diethyl ether, blood, liver and visceral fat (epididymal fat, perirenal fat, mesenteric fat and retroperitoneal fat) were taken and weighed after washing with 0.1M PBS (pH 7.4). Blood taken from the abdominal aorta was centrifuged at 1000×g for 15 minutes for the separation of plasma.

2) Changes of Body and Visceral Fat-Pad Weights

Figure 8:
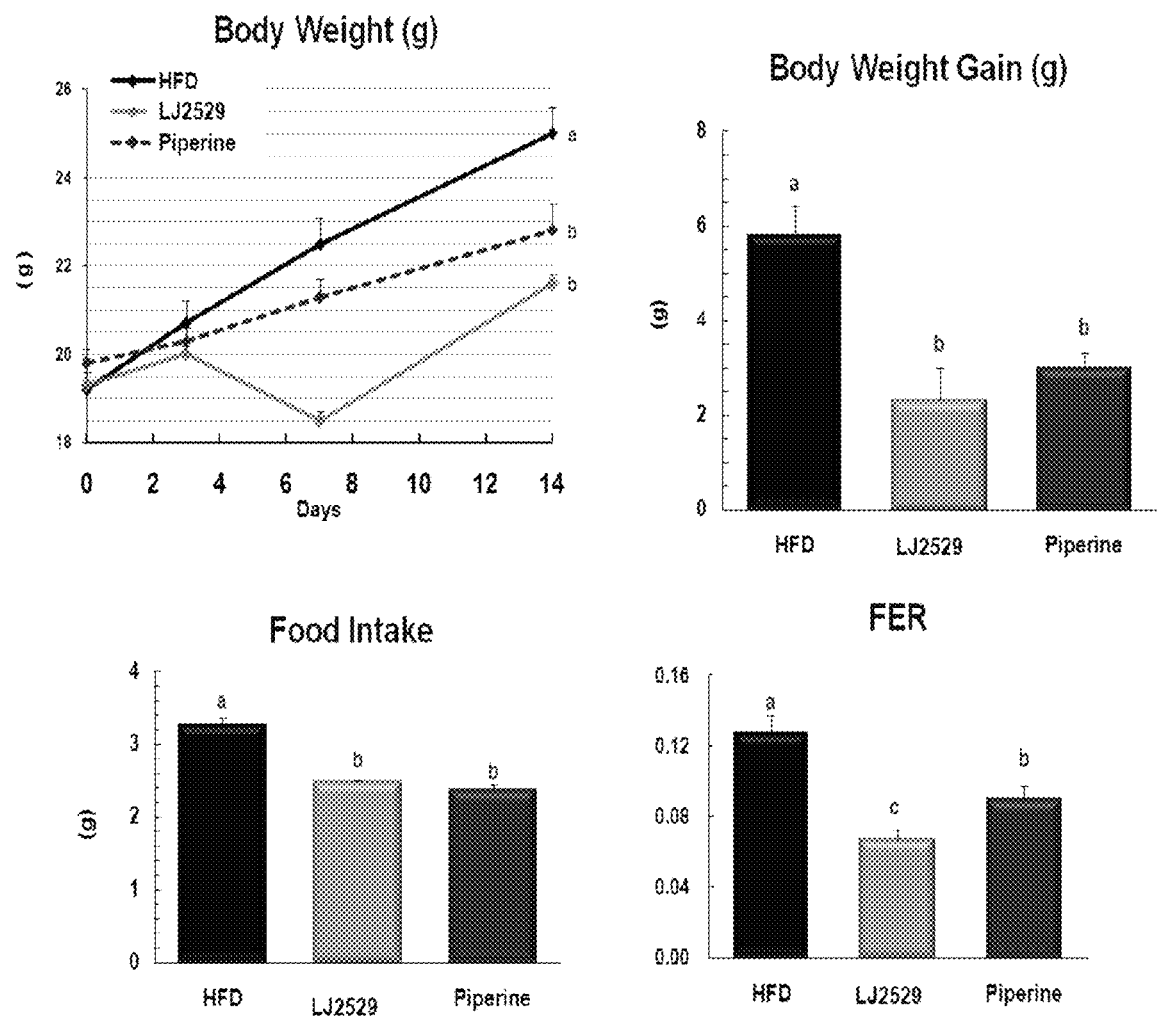
FIG. 8 represent body weight gain, daily food intake and feed efficiency ratio of mice fed with test diets (JL-2529).

After feeding the test diet for 14 weeks, the LJ-2529-supplemented group showed significant decrease of body weight gain by 60% as compared to HFD. Therefore, LJ-2529 compound has excellent effects to reduce body weights as compared to piperine (−48%). The daily food intake of LJ-2529 and piperine-supplemented group showed decrease by 24% and 27%, respectively. The FER of LJ-2529-supplemented group was decreased by 60% compared with HFD, which is lower than piperine (FIG. 8). The LJ-2529-supplemented group showed significantly reduced weights of the epididymal, perirenal, mesenteric fat-pad, and retroperitoneal fat-pad as compared to HFD. The total visceral fat weight was significantly reduced by 15% than in the HFD group (P<0.001) (FIGS. 3 and 4). Accordingly, it would be appreciated that LJ-2529 compound has excellent effects to reduce body weights and visceral fat-pad weights.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for treating or ameliorating a metabolic disease selected from the group consisting of obesity, type 2 diabetes, dyslipidemia, fatty liver, and insulin resistance syndrome, comprising administering to a subject a composition containing a piperidine derivative represented by Chemical Formula 1 or 2 below as an active ingredient:

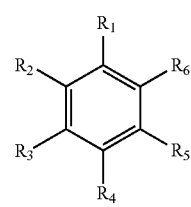

Chemical Formula 1 wherein, in Chemical Formula 1, $R_1$-$R_5$ are each independently hydrogen, $C_1$-$C_5$ alkyl or $C_1$-$C_5$ alkoxy, and $R_2$ and $R_3$ are optionally linked to each other to form a ring structure;

R$_2$ and R$_3$, when being linked to each other to form the ring structure, forms a heterocyclic structure including two oxygen atoms as heteroatoms; and
R$_6$ is

wherein m is an integer of 1 or 2 and n is an integer of 1 or 2; R$_7$ is C$_1$-C$_5$ alkyl or piperidine; X is oxygen or sulfur; and R$_8$ is C$_1$-C$_5$ alkyl; and

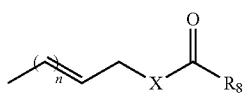

R$_6$ is

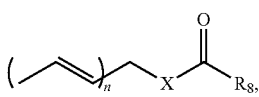

when R$_2$ and R$_3$ are linked to each other to form the ring structure, and

Chemical Formula 2

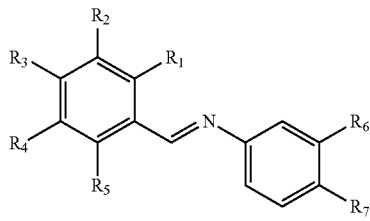

wherein, in Chemical Formula 2, R$_1$-R$_5$ are each independently hydrogen, C$_1$-C$_5$ alkyl, C$_1$-C$_5$ alkoxy, or halogen, R$_3$ and R$_4$ are optionally linked to each other to form a ring structure, and R$_4$ and R$_5$ are optionally linked to each other to form a ring structure;
R$_3$ and R$_4$, when being linked to each other to form the ring structure, form a heterocyclic structure including two oxygen atoms as heteroatoms;
R$_4$ and R$_5$, when being linked to each other to form the ring structure, form a heterocyclic structure including two oxygen atoms as heteroatoms;
R$_6$ and R$_7$ are each independently hydrogen or C$_1$-C$_5$ alkyl, and R$_6$ and R$_7$ are optionally linked to each other to form ring structure; and
R$_6$ and R$_7$, when being linked to each other to form the ring structure, form a heterocyclic structure including two nitrogen atoms as heteroatoms.

2. The method of claim 1, wherein, in Chemical Formula 1, R$_1$-R$_5$ are each independently hydrogen, C$_1$-C$_5$ alkyl, or C$_1$-C$_2$ alkoxy.

3. The method of claim 1, wherein, in Chemical Formula 1, R$_2$ and R$_3$ are linked to each other to form a ring structure; the ring structure forms a heterocyclic structure containing two oxygen atoms as heteroatoms; and the heterocyclic structure is dioxolane.

4. The method of claim 1, wherein, in Chemical Formula 2, R$_1$-R$_5$ are each independently hydrogen or halogen.

5. The method of claim 1, wherein, in Chemical Formula 2, R$_3$ and R$_4$ are linked to each other to form a ring structure; the ring structure forms a heterocyclic structure containing two oxygen atoms as heteroatoms; and the heterocyclic structure is dioxolane.

6. The method of claim 1, wherein, in Chemical Formula 2, R$_4$ and R$_5$ are linked to each other to form a ring structure; the ring structure forms a heterocyclic structure containing two oxygen atoms as heteroatoms; and the heterocyclic structure is dioxolane.

7. The method of claim 1, wherein, in Chemical Formula 2, R$_6$ and R$_7$ are linked to each other to form a ring structure; the ring structure forms a heterocyclic structure containing two nitrogen atoms as heteroatoms; and the heterocyclic structure is imidazolone or imidazolethione.

8. The method of claim 1, wherein the piperine derivative is a compound selected from the group consisting of compounds represented by Chemical Formulas 3, 4, and 6-15 below:

Chemical Formula 3

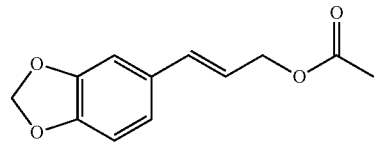

Chemical Formula 4

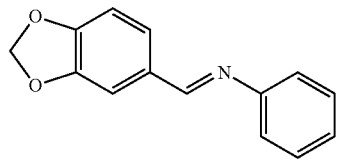

Chemical Formula 6

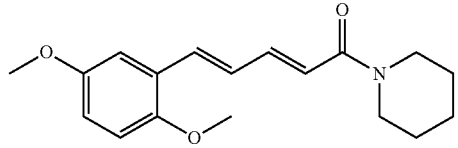

Chemical Formula 7

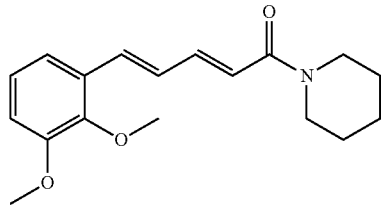

Chemical Formula 8

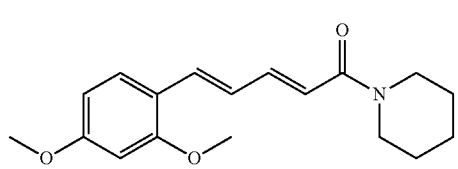

-continued
Chemical Formula 9
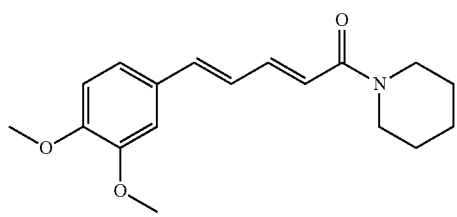
Chemical Formula 10
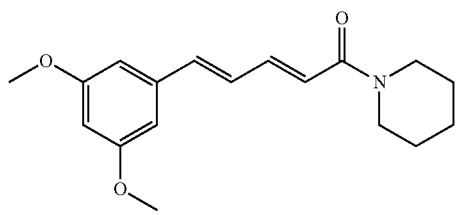
Chemical Formula 11
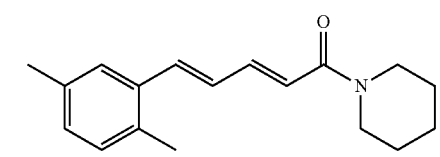
Chemical Formula 12
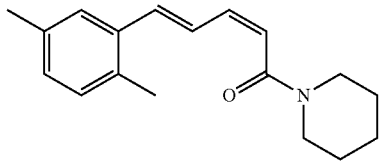
-continued
Chemical Formula 13
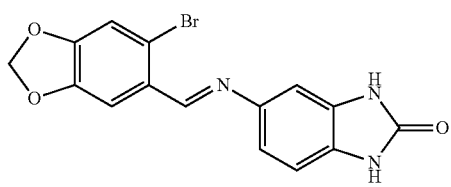
Chemical Formula 14
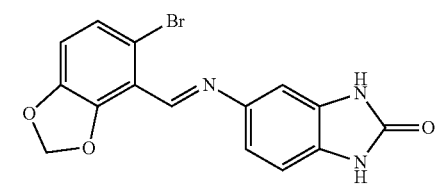
Chemical Formula 15
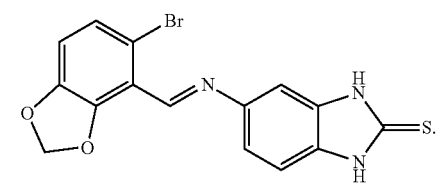
9. The method of claim 1, wherein the dyslipidemia is hyperlipidemia.
* * * * *